US006574495B1

(12) United States Patent
Golman et al.

(10) Patent No.: US 6,574,495 B1
(45) Date of Patent: Jun. 3, 2003

(54) PARA-HYDROGEN LABELLED AGENTS AND THEIR USE IN MAGNETIC RESONANCE IMAGING

(75) Inventors: Klaes Golman, Malmo (SE); Oskar Axelsson, Malmo (SE); Haukur Johanneson, Malmo (SE); Charlotte Olofsson, Malmo (SE); Sven Mansson, Malmo (SE); Stefan Petersson, Malmo (SE)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/565,450

(22) Filed: May 5, 2000

Related U.S. Application Data

(63) Continuation of application No. PCT/GB98/03399, filed on Nov. 12, 1998.
(60) Provisional application No. 60/066,570, filed on Nov. 26, 1997, and provisional application No. 60/076,924, filed on Mar. 5, 1998.

(30) Foreign Application Priority Data

Nov. 12, 1997 (GB) .............................................. 9723920
Jan. 5, 1998 (GB) .............................................. 9800158

(51) Int. Cl.[7] .................................................. A61B 5/05
(52) U.S. Cl. ...................... 600/420; 600/407; 600/410; 324/307; 324/309; 424/9.3
(58) Field of Search ................................. 600/407, 410, 600/420; 324/307, 309; 424/9.3

(56) References Cited

U.S. PATENT DOCUMENTS 5,700,448 A * 12/1997 Golman et al. .............. 424/9.3

FOREIGN PATENT DOCUMENTS

WO          0 665 282 A       8/1995

OTHER PUBLICATIONS

Casanova et al., "phenylacetylene–1–13C", Organic Preparations and Procedures, 1969, XP002094734.
Baldwin et al., "Synthesis of chiral isoxazolidin–5–ones and their applications to the synthesis of beta–amino–alanines and beta-(N–hydroxyamino)–alanines", Tetrahedron, 1994, XP002094735.
Jordan et al., "Mechanistic and stereochemical investigation of fatty acid and polyketide biosynthesis using chiral malonates", Tetrahedron, 1991, XP002094736.
Bottomley P.A. et al., "Proton–decoupled, Overhauser–enhanced, Spatially Localized Carbon–13 Spectroscopy in Humans*", Magnetic Resonance in Medicine, Dec. 1, 1989, XP000102293.
Barkemeyer et al., "Hetero–NMR enhancement via parahydrogen", J. Am. Chem. Soc., 1995, XP002094737.
"Ortho– and Parahydrogen: Spin Isomers of Molecular Hydrogen" http://www.thch.uni–bonn.de/pc/bargon/PHIP/parahydrogen.html Feb. 5, 2002.*
Golman et al. "Parahydrogen–Induced Polarization in Imaging: Subsecond 13 C Angiography" Magnetic Resonance in Medicine 46:1–5 (2001).*
Koch et al. "Examination of Subsequent Reaction Products Enhanced Through Parahydrogen–Induced Nuclear Polarization (PHIP)" Magnetic Resonance in Chemistry 2000; vol. 38: p. 216–220.*

* cited by examiner

Primary Examiner—Marvin M. Lateef
Assistant Examiner—Jeoyuh Lin
(74) Attorney, Agent, or Firm—Bacon & Thomas

(57) ABSTRACT

The invention provides a method of magnetic resonance investigation of a sample, said method comprising: (i) reacting para-hydrogen enriched hydrogen with a hydrogenatable MR imaging agent precursor containing a non-hydrogen non-zero nuclear spin nucleus to produce a hydrogenated MR imaging agent; (ii) administering said hydrogenated MR imaging agent to said sample; (iii) exposing said sample to radiation of a frequency selected to excite nuclear spin transitions of said non-zero nuclear spin nucleus in said hydrogenated MR imaging agent; (v) detecting magnetic resonance signals of said non-zero nuclear spin nucleus from said sample; and (vi) optionally, generating an image or biological functional data or dynamic flow data from said detected signals.

22 Claims, 11 Drawing Sheets

PARA-HYDROGEN LABELLED AGENTS AND THEIR USE IN MAGNETIC RESONANCE IMAGING

This application is a continuation of pending international application number PCT/GB98/03399 filed Nov. 12, 1998 (of which the entire disclosure of the pending, prior application is hereby incorporated by reference), which itself is a continuation-in-part of U.S. provisional applications Nos. 60/066,570, filed Nov. 26, 1997; and 60/076,924, filed Mar. 5, 1998.

This invention relates to a method of magnetic resonance imaging (MRI) in particular to non-proton magnetic resonance imaging, especially of nuclei with I (nuclear spin)=½, e.g. $^{13}C$, $^{15}N$ and $^{29}Si$.

Magnetic resonance imaging is a diagnostic technique that has become particularly attractive to physicians as it is non-invasive and does not involve exposing the patient under study to potentially harmful radiation such as X-rays.

In order to achieve effective contrast between MR images of different tissue types, it has long been known to administer to the subject MR contrast agents (e.g. paramagnetic metal species) which affect relaxation times in the zones in which they are administered or at which they congregate. By shortening the relaxation times of the imaging nuclei (the nuclei whose MR signal is used to generate the image) the strength of the MR signal is changed and image contrast is enhanced.

MR signal strength is also dependent on the population difference between the nuclear spin states of the imaging nuclei. This is governed by a Boltzmann distribution and is dependent on temperature and magnetic field strength. However, in MR imaging contrast enhancement has also been achieved by utilising the "Overhauser effect" in which an esr transition in an administered paramagnetic species is coupled to the nuclear spin system of the imaging nuclei. The Overhauser effect (also known as dynamic nuclear polarisation) can significantly increase the population difference between excited and ground nuclear spin states of the imaging nuclei and thereby amplify the MR signal intensity. Most of the Overhauser contrast agents disclosed to date are radicals which are used to effect polarisation of imaging nuclei in vivo. There is very little reported work on techniques which involve ex vivo polarisation of imaging nuclei prior to administration and MR signal measurement.

U.S. Pat. No. 5,617,859 (Souza) discloses a magnetic resonance imaging system employing a small, high-field polarizing magnet (e.g. a 15 T magnet) to polarize a frozen material which is then warmed up and administered to a subject placed within the imaging apparatus. The material used may be water, saline, a fluorocarbon or a noble gas such as He or Xe. Since the magnetic field in the polarizing magnet is greater than that inside the imaging apparatus and since polarization is effected at low temperature, an increased population difference between the nuclear spin states (i.e. polarization) should result in a stronger MR signal from the polarized material.

In U.S. Pat. No. 5,611,340 (Souza), a somewhat similar MR imaging system is disclosed. Here however liquid hydrogen is polarized by the polarizing magnet and thereafter it is heated up and reacted with oxygen to produce polarized water which is administered to the subject. The resulting enhanced MR signal will be an enhanced $^1H$ MR signal.

U.S. Pat. No. 5,545,396 (Albert) discloses an in vivo MR imaging method in which a noble gas (e.g. $^{129}Xe$ or $^3He$) having a hyperpolarised nuclear spin is inhaled into the lungs and a representation of its spatial distribution therein is generated. MR imaging of the human oral cavity using hyperpolarised $^{129}Xe$ was also reported by Albert in J. Mag. Res., 1996: B111, 204–207.

The use of hyperpolarised MR contrast agents in MR investigations such as MR imaging has the advantage over conventional MR techniques in that the nuclear polarisation to which the MR signal strength is proportional is essentially independent of the magnetic field strength in the MR apparatus. Currently the highest obtainable field strengths in MR imaging apparatus are about 8 T, while clinical MR imaging apparatus are available with field strengths of about 0.2 to 1.5 T. Since superconducting magnets and complex magnet construction are required for large cavity high field strength magnets, these are expensive. Using a hyperpolarised contrast agent, since the field strength is less critical it is possible to make images at all field strengths from earth field (40–50 $\mu T$) up to the highest achievable fields. However there are no particular advantages to using the very high field strengths where noise from the patient begins to dominate over electronic noise (generally at field strengths where the resonance frequency of the imaging nucleus is 1 to 20 MHz) and accordingly the use of hyperpolarised contrast agents opens the possibility of high performance imaging using low cost, low field strength magnets.

The present invention is based on a method of MRI of a sample which relies on ex vivo nuclear polarisation of selected non-hydrogen, I≠0 imaging nuclei (e.g. $^{13}C$, $^{15}N$ and $^{29}Si$ nuclei) of an MR imaging agent by reaction of a precursor to said agent with para-hydrogen enriched hydrogen gas.

Thus viewed from one aspect the present invention provides a method of magnetic resonance investigation of a sample, preferably a human or non-human animal body (e.g. a mammalian, reptilian or avian body), said method comprising:

(i) reacting para-hydrogen enriched hydrogen with a hydrogenatable MR imaging agent precursor containing a non-zero nuclear spin nucleus other than $^1H$ to produce a hydrogenated MR imaging agent;

(ii) administering said hydrogenated MR imaging agent to said sample;

(iii) exposing said sample to radiation of a frequency selected to excite nuclear spin transitions of said non-zero nuclear spin nucleus in said hydrogenated MR imaging agent;

(iv) detecting magnetic resonance signals of said nonzero nuclear spin nucleus from said sample; and (v) optionally, generating an image or biological functional data or dynamic flow data from said detected signals.

The MR signals obtained in the method of the invention may be conveniently converted into 2- or 3-dimensional image data or into functional, flow or perfusion data by conventional manipulations.

Hydrogen molecules exist in two different forms, namely para-hydrogen (p-$H_2$) where the nuclear spins are antiparallel and out of phase (the singlet state) and ortho hydrogen (o-$H_2$) where they are parallel or antiparallel and in phase (the triplet state). At room temperature, the two forms exist in equilibrium with a 1:3 ratio of para:ortho hydrogen. At 80K the ratio is 48:52 and at 20K it approaches 100:0, i.e. 99.8:0.2. Reducing the temperature still further is not beneficial since hydrogen freezes at about 17K. The rate of equilibration is very low in pure hydrogen but in the presence of any of several known catalysts (such as $Fe_3O_4$, $Fe_2O_3$, or activated charcoal) an equilibrium mixture is rapidly obtained and remains stable at room temperature for several hours after separation from the catalyst. Thus by "enriched hydrogen" above is meant hydrogen in which there is a higher than equilibrium proportion of para-hydrogen, for example where the proportion of para- hydrogen is more than 25%, preferably more than 30%, preferably 45% or more, more preferably 60% or more, particularly preferably 90% or more, especially preferably 99% or more. Typically the preparation of enriched hydrogen, an optional initial step in the method according to the invention, will be carried out catalytically at low temperatures e.g. at 160K or less, preferably at 80K or less or more preferably at about 20K.

The parahydrogen thus formed may be stored for long periods, preferably at low temperature, e.g. 18–20° K. Alternatively it may be stored in pressurized gas form in containers with non-magnetic and non-paramagnetic inner surfaces, e.g. a gold or deuterated polymer coated container.

Generally speaking, if a p-$H_2$ molecule is transferred to a host molecule by means of catalytic hydrogenation (optionally at elevated pressure (e.g. 50 to 100 bar)), the proton spins remain antiparallel and begin to relax to thermal equilibrium with the normal time constant $T_1$ of the hydrogen in the molecule (typically about one second). However during relaxation some of the polarisation may be transferred to neighbouring nuclei by cross-relaxation or other types of coupling. The presence of, for example, a $^{13}C$ nucleus with a suitable substitution pattern close to the relaxing hydrogen may lead to the polarisation being conveniently trapped in the slowly relaxing $^{13}C$ nucleus. An enhancement factor of 2580 has been reported in the literature (Barkemeyer et al, 1995, J Am Chem Soc 117, 2927–2928). A $^{13}C$ nucleus in a carbonyl group or in certain quaternary carbons may have a $T_1$ relaxation time typically of more than a minute.

The hydrogenation step should preferably be performed in the liquid or gaseous phase, preferably in the absence of materials which would promote relaxation. If in the liquid phase, then the catalyst can be removed by filtration through, for example, an ion-exchange resin. If in the gas phase, then separation of a solid catalyst is trivial and the MR imaging agent formed can simply be passed into a suitable solvent, preferably a physiologically tolerable solvent, most preferably water, and used according to the invention.

Thus the present invention is based on the recognition that polarisation of certain nuclei (e.g. $^{13}C$ nuclei) in a host molecule using enriched hydrogen represents a means for performing ex vivo polarisation of an MR imaging agent prior to its administration into a subject and conventional MR imaging. The term "MR imaging agent" used herein refers to an agent containing nuclei (MR imaging nuclei) capable of emitting magnetic resonance signals. Such MR imaging nuclei are non-zero nuclear spin nuclei capable of emitting magnetic resonance signals, preferably I=½ nuclei (other than hydrogen itself), such as e.g. $^{19}F$, $^3Li$, $^1H$, $^{13}C$, $^{15}N$, $^{29}Si$ or $^{31}P$ nuclei, but preferably are $^{13}C$ or $^{15}N$ nuclei, most preferably $^{13}C$ nuclei. In other words, the MR imaging agent precursor should preferably contain a non-hydrogen I=½ nucleus.

The non hydrogen non zero nuclear spin nucleus in the MR imaging agent may be present in its naturally occurring isotopic abundance. However where the nucleus is a non-preponderant isotope (e.g. $^{13}C$ where $^{12}C$ is the preponderant isotope) it will generally be preferred that the content of the nucleus be enriched, ie. that it is present at a higher than normal level.

Thus viewed from a further aspect the present invention provides the use of hydrogen (e.g. para-hydrogen enriched hydrogen) in MR imaging of a sample (e.g. a human body), preferably $^{13}C$, or $^{15}N$ MR imaging of a sample.

Viewed from an alternative aspect, the invention provides the use of para-hydrogen enriched hydrogen for the manufacture of an MR imaging agent for use in a method of diagnosis involving generation of an MR image by non $^1H$ MR imaging of a human or non-human animal body.

Viewed from a still further aspect the invention provides use of a hydrogenatable compound containing a non hydrogen non-zero nuclear spin nucleus in the manufacture of an MR imaging agent for use in a method of diagnosis involving generation of an MR image by non-proton MR imaging, said manufacture involving hydrogenation of said compound with para-hydrogen enriched hydrogen.

By imaging, it will be appreciated that not just production of two or three dimensional morphological images is covered: the images produced may be representations of the value or temporal change in value of a physiological parameter such as temperature, pH, oxygen tension, etc. Morphological images however will generally be produced.

MR imaging agent precursors suitable for use in the present invention are hydrogenatable and will typically possess one or more unsaturated bonds, e.g. double or triple carbon-carbon bonds. For in vivo imaging, the hydrogenated MR imaging agent should of course be physiologically tolerable or be capable of being presented in a physiologically tolerable form.

The MR imaging agent should preferably be strongly polarisable (for example, to a level of greater than 5%, preferably greater than 10%, more preferably greater than 25%) and have a non-hydrogen MR imaging nucleus with a long $T_1$ relaxation time under physiological conditions, e.g. $^{13}C$, $^{15}N$ or $^{29}Si$. By a long $T_1$ relaxation time is meant that $T_1$ is such that once polarised, the MR imaging agent will remain so for a period sufficiently long to allow the imaging procedure to be carried out in a comfortable time span. Significant polarisation should therefore be retained for at least 1 s, preferably for at least 60 s, more preferably for at least 100 s and especially preferably 1000 s or longer.

There will preferably be nuclear spin:spin coupling in the imaging agent between the MR imaging nucleus and at least one of the hydrogens introduced as a result of hydrogenation with para-hydrogen. The coupling constant is preferably between 1 and 300 Hz, more preferably between 10 and 100 Hz. This is preferably achieved by placing the MR imaging nucleus no more than 3, more preferably no more than 2 bonds away from the para-hydrogen derived hydrogen. Desirably the nmr signal from the MR imaging nucleus (hereinafter occasionally referred to as the reporter nucleus), is sharp, preferably with a linewidth (at 37° C. in blood or tissue) of less than 100 Hz, more preferably less than 10 Hz, even more preferably less than 1 Hz. Accordingly, the MR imaging agent will preferably contain as few non-zero nuclear spin atoms (besides the reporter nucleus and the two protons from the p.$H_2$) as possible which can couple with the reporter nucleus. Desirably therefore the MR imaging agent contains no more than 10, more preferably no more than 5, still more preferably no more than 2, even more preferably no more than 1, and especially preferably no non-zero nuclear spin nuclei within 3 bonds of the reporter nucleus, and still more preferably within 4 bonds. Most preferably the only non-zero nuclear spin nuclei in the MR imaging agent are the reporter nucleus and the protons from the p.$H_2$. Quadrupolar nuclei (e.g. $^{14}N$, $^{35}Cl$ and $^{79}Br$) should preferably not be included in the MR imaging agent although they may be present in counterions or other dissolved components of a contrast medium containing the MR imaging agent. Avoidance of undesired nuclei may involve use of deuterium in place of protons in the MR imaging agent. Thus where the unsaturated bond to be hydrogenated is a C=C bond, this may desirably be in a —CD=CD— structure. In this way the polarization transfer to the reporter nucleus, e.g. $^{13}$C in a —$^{13}$C—C=C— structure may be increased. The MR imaging agent should preferably be relatively small (e.g. molecular weight less than 500 D, more preferably less than 300 D (e.g. 50–300 D) and more preferably 100 to 200 D) and also preferably should be soluble in a liquid solvent or solvent mixture, most preferably in water or another physiologically tolerable solvent or solvent mixture. The MR imaging agent precursor likewise is preferably soluble in such solvents or solvent mixtures and desirably is capable of undergoing rapid catalysed hydrogenation, e.g. at a conversion rate of at least 1 g precursor/min using 2 mole % or less of catalyst. Furthermore, the chemical shift, or even better the coupling constant of the nmr signal from the imaging nucleus in the MR imaging agent should preferably be influenced by physiological parameters (e.g. morphology, pH, metabolism, temperature, oxygen tension, calcium concentration, etc). For example, influence by pH can be used as a general disease marker, whilst influence by metabolism may be a cancer marker. Alternatively, the MR imaging agent may conveniently be a material which is transformed (e.g. at a rate such that its half life is no more than $10 \times T_1$ of the reporter nucleus, preferably no more than $1 \times T_1$) in the subject under study to a material in which the reporter nucleus has a different coupling constant or chemical shift. In this case the subject may be inanimate or animate, e.g. a human or animal, a cell culture, a membrane-free culture, a chemical reaction medium, etc. Thus for example the reporter nucleus may provide information on the operation of the biochemical machinery of an organism where that machinery transforms the MR imaging agent and in so doing changes the chemical shift or coupling constant of the reporter nucleus. It will be appreciated that the imaging process used in this case may be an nmr spectroscopic procedure rather than (or in addition to) an imaging procedure which generates a morphological image.

The MR imaging agent should preferably be $^{13}$C or $^{15}$N enriched, particularly preferably $^{13}$C enriched, in positions close to the hydrogenation site, e.g. a double or triple bond, and where relaxation is slow. Preferred MR imaging agents according to the invention also exhibit the property of low toxicity.

Generally speaking, to increase the MR signal from the hydrogenated MR imaging agent, it may be desirable to incorporate more than one unsaturated bond in each molecule of the precursor, e.g. in a conjugated unsaturated system. However due consideration must be given to the need to keep molecular weight relatively low to prevent difficulties in administration of the agent. The presence of one or more C=C bonds in the hydrogenatable MR imaging agent precursor increases the reaction rate and may therefore be preferred. Also preferred are compounds with an unsaturated carbon-carbon bond with one or more carbonyl substituents, e.g. an αβ unsaturated carbonyl compound. Particularly preferred are compounds comprising disubstituted unsymmetric alkylene or acetylene groups with a carbonyl-unsaturation-carbonyl moiety. Such compounds are of high reactivity and may allow two or more $^{13}$C atoms to be incorporated to utilize the polarisation more efficiently.

Precursors that match as many of the above design parameters as possible have been found to form excellent MR imaging agents once reacted with parahydrogen. Such agents have both in vitro and in vivo usage. Such MR imaging agents and their precursors which are reporter nucleus enriched, ie. have greater than natural isotopic abundance of the reporter nucleus, are novel and form further aspects of the invention. Viewed from a first of these aspects the invention provides a precursor compound:

(i) containing a hydrogenatable unsaturated bond;
(ii) containing a non-hydrogen non zero nuclear spin nucleus at greater than natural isotopic abundance;
(iii) having a molecular weight preferably below 1000 D, more preferably below 500 D; and
(iv) which following hydrogenation has an nmr spectrum for said non-hydrogen non zero nuclear spin nucleus which is a multiplet having a coupling constant relative to one of the hydrogens introduced by hydrogenation of 1 to 300 Hz and having a linewidth of less than 100 Hz, preferably below 10 Hz, more preferably below 1 Hz.

The hydrogenatable precursor compound of the invention Preferably contains as said non-hydrogen non zero nuclear spin nucleus a I=½ nucleus such as $^{13}$C, $^{15}$N or $^{29}$Si, especially $^{13}$C. Preferably it also has some or all of the desired properties discussed earlier, e.g. solubility, pavcity of other I≠0 nuclei (although these may be present in a counterion component of the compound if it is ionic), reactivity to hydrogenation, etc.

Viewed from a further aspect the invention also provides a reporter compound:

(i) containing at least two protons;
(ii) containing a non-hydrogen non zero nuclear spin nucleus at greater than natural isotopic abundance;
(iii) having a molecular weight preferably below 000 D, more preferably below 500 D; and
(iv) having an nmr spectrum for said non-hydrogen non zero nuclear spin nucleus which is a multiplet having a coupling constant relative to one of said at least two protons 1 to 300 Hz and having a linewidth of less than 100 Hz, preferably below 10 Hz, more preferably below 1 Hz.

Once again, the reporter compounds of the invention, which are obtainable by hydrogenation of the precursor compounds of the invention will desirably possess some or all of the desired properties referred to earlier, e.g. solubility, narrow linewidths, coupling constants in the 10 to 100 Hz range, coupling constant sensitivity, chemical shift sensitivity, isotopic make up, etc.

Preferred-precursor compounds for MR imaging agents for use according to the invention desirably contain the following molecular sub-units:

(i) at least one C=C or C≡C bonds;
(ii) a C, N or Si atom separated by one or two bonds from a C=C or C≡C bond, bound only to atoms the naturally most abundant isotope form of which has a nuclear spin I=0, and not coupled by a series of covalent bonds to any atoms the naturally most abundant isotopic form of which has I>½; and
(iii) at least one water-solubilizing moiety, ie. a functional group which imparts water solubility to the molecule, e.g. hydroxyl, amine or cxyacid (e.g. carboxyl) groups.

Correspondingly, preferred MR imaging agents for use according to the invention desirably contain the following molecular sub-units:

(i) at least one CH—CH or CH=CH moiety;
(ii) a C, N or Si atom separated by one or two bonds from a CH—CH or CH=CH moiety, bound only to atoms the naturally most abundant isotopic form of which has I=0, and not coupled by a series of covalent bonds to any atoms the naturally most abundant isotopic form of which has I>½; and (iii) at least one water-solubilizing moiety, ie. a functional group which imparts water solubility to the molecule, e.g. hydroxyl, amine or oxyacid (e.g. carboxyl) groups.

While compounds meeting these criteria can be used according to the invention without enrichment in $^{13}C$, $^{15}N$ or $^{29}Si$, it is preferred that they be enriched and in particular that there be such isotopic enrichment of the atoms defined by criterion (ii).

Specifically preferred hydrogenatable MR imaging agent precursors for use in the method of the invention include simple unsaturated acids (e.g. acrylic acid, crotonic acid, propionic acid, fumaric acid, maleic acid and $HOOC.C\equiv C.COOH$), especially where a carboxyl carbon separated by two or more favourably one bond from the unsaturated bond is $^{13}C$ or $^{13}C$ enriched,

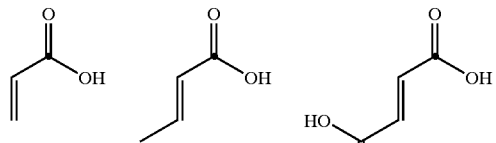

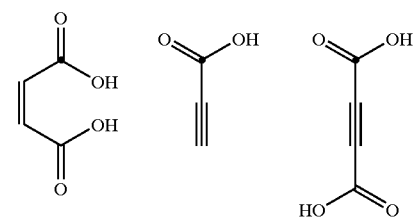

unsaturated quaternary carbon compounds where the quaternary carbon is separated by two or more preferably one bond from the unsaturated bond and preferably where the quaternary carbon is $^{13}C$ or $^{13}C$ enriched, e.g.

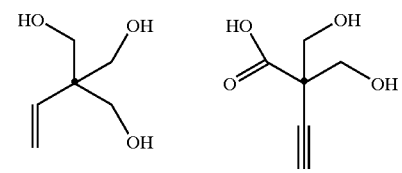

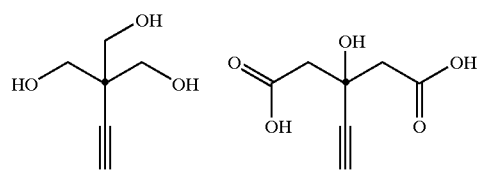

compounds with more than one hydrogenation site such as

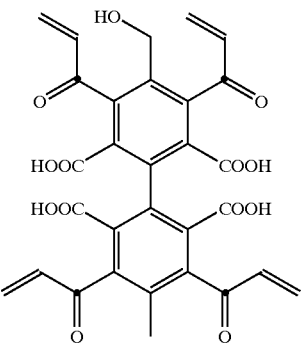

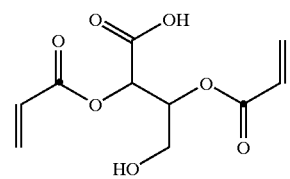

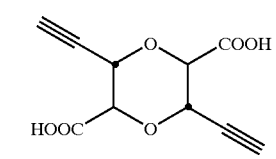

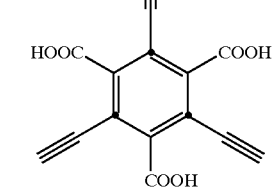

especially where a carbon separated by two or more preferably one bond from an unsaturated bond is $^{13}C$ or $^{13}C$ enriched and other compounds such as:

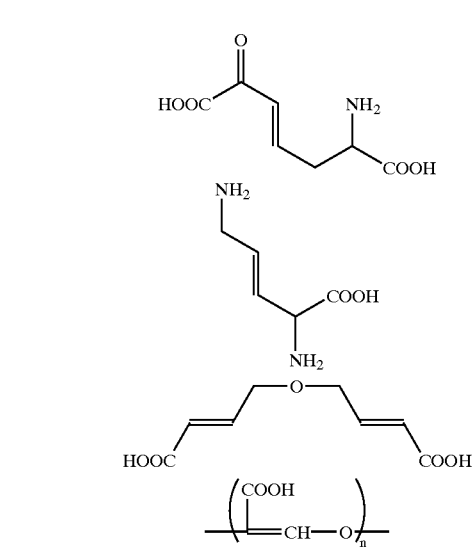

and

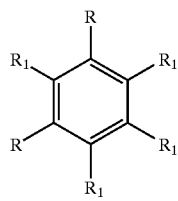

(where $R_1$ is

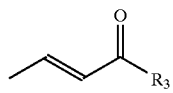

$R_3$ is alkyl, hydroxyalkyl, amino, hydroxyl etc, R is $CONHR_2$ and $R_2$ is a conventional hydrophilic group known to be useful in X-ray contrast media such as a straight chain or branched $C_{1-10}$-alkyl group, preferably a $C_{1-5}$ group, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms).

$^{13}C$ enriched MR imaging agents have $^{13}C$ at one particular position (or more than one particular position) in an amount in excess of the natural abundance, i.e above about 1%. Preferably such a single carbon position will have 5% or more $^{13}C$, particularly preferably 10% or more, especially preferably 25% or more, more especially preferably 50% or more, even more preferably in excess of 99% (eg 99.9%).

In all these hydrogenatable compounds represented by formulae herein, protons (H) are Preferably replaced by deuterons, except perhaps protons which are labile on dissolution (e.g. carboxyl protons).

In addition, compounds which on hydrogenation yield compounds which are or are analogous to naturally occurring biomolecules (e.g. amino acids, metabolites, neurotransmitters, etc) are possible MR imaging agent precursors for use in the method of the invention.

For studies of biochemical reactions, it may also be interesting to use succinic acid (which occurs in the citric acid cycle), especially $^{13}C$ enriched succinic acid:

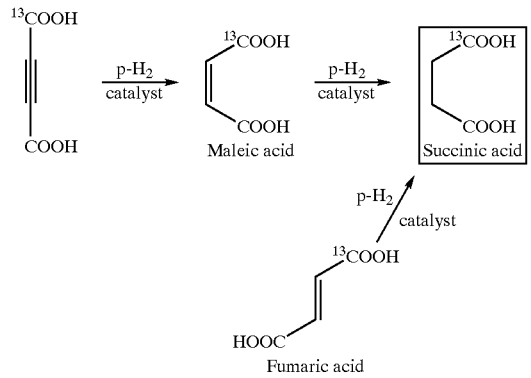

For studies of peptide/protein synthesis, whether natural or artificial, it may likewise be interesting to use amino acids, produced by pH$_2$ hydrogenation of a β carbon-γ carbon unsaturated bond, especially where the carboxyl carbon is $^{13}C$ enriched.

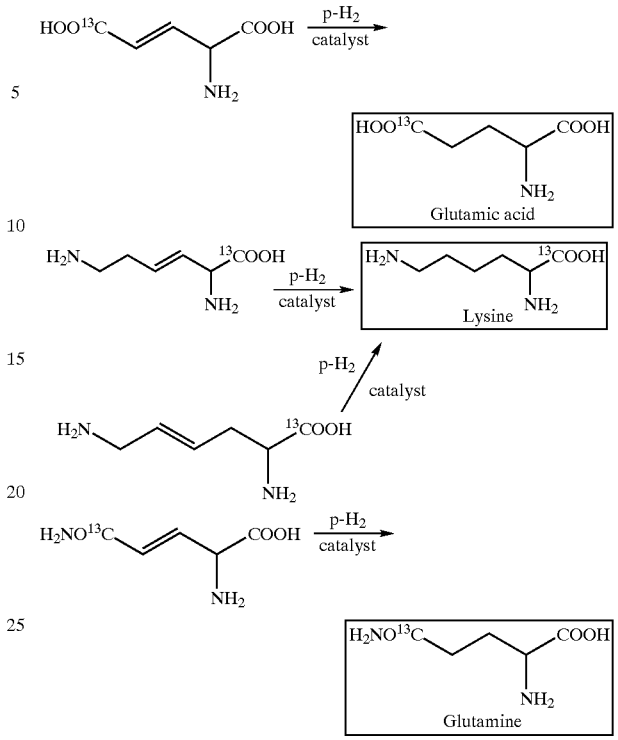

Amides, amines, cyanides and nitroxides or other nitrogen containing MR imaging agents are particularly suitable for $^{15}N$ reporter nuclei as are compounds which comprise a ring nitrogen containing heterocycle. One example of a $^{15}N$ reporter nucleus imaging agent is acetyl choline, which is biologically modified and so may be used to study metabolic processes. This imaging agent may be produced by pH$_2$ hydrogenation of corresponding ethylenically or acetylenically unsaturated precursors, preferably ones enriched in $^{15}N$:

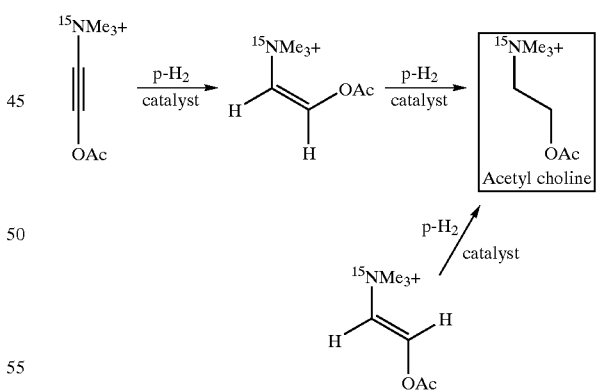

Likewise amino acids, especially deuterated versions thereof may be used as vehicles for $^{15}N$. Silane and silicone compounds may similarly be used as vehicles for $^{29}Si$.

Due to their biotolerability, compounds with quaternary carbons may be preferred. Cationic compounds may also be used, e.g. quaternary ammonium salts.

One especially preferred hydrogenatable or hydrogenated MR imaging agent is maleic acid dimethyl ester which is the hydrogenation product of acetylene dicarboxylic acid dimethyl ester.

Another useful MR imaging agent would be methionine, and thus an unsaturated methionine precursor may advantageously be used as the precursor compound.

Other interesting precursors include acetylenic compounds such as the following

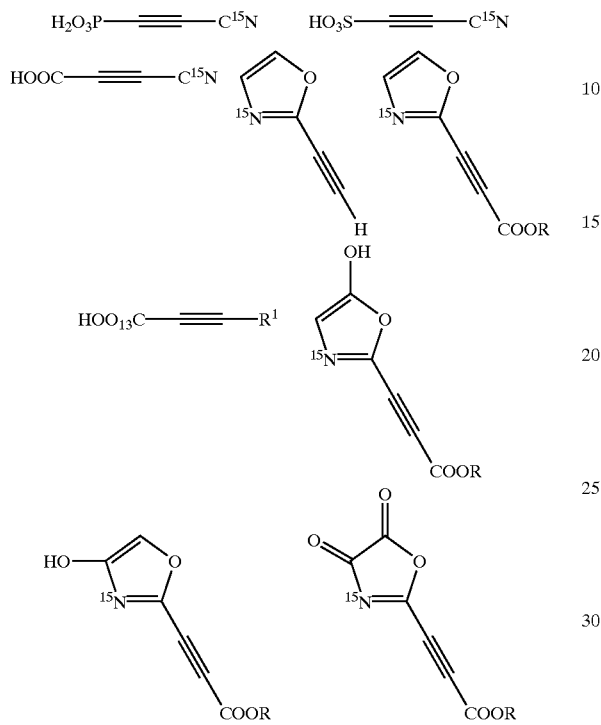

where R is H or $C_{1-6}$ alkyl and $R^1$ is hydroxylalkyl, or a sulphone or sulphoxide.

Typically the hydrogenatable MR imaging agent precursor will undergo hydrogenation in the presence of a suitable catalyst, optionally at elevated temperature or pressure. The hydrogenation catalyst used in the method of the invention need not be a homogeneous catalyst but during hydrogenation the entire hydrogen molecule should be transferred to the host molecule. Some examples of catalysts that are able to fulfil this criterion are shown in Table 1.

TABLE 1

Hydrogenation catalysts that transfer dihydrogen to a double or triple bond

| Catalyst | Synonym | Water Solubility | Comment |
|---|---|---|---|
| $(PPh_3)\ RhCl$ | Wilkinson's catalyst | – | Active when bound to zeolite (12Å) |
| $[(NBD)\ Rh\ (Amphos)_2]^{3+}$ | | + | Cationic |
| $(TPPMS)_3RhCl$ | | + | Anionic |
| $(HEXNa)_2RhCl$ | | + | Anionic |
| $(OCTNa)_2RhCl$ | | + | Anionic |
| $IrCl(CO)\ (PPh_3)_2$ | Vasca's complex | – | |
| (bicycio [2.2.1] hepta-2, 5-diene) [1,4-bis (diphenylphosphino) butane] rhodium (I) tetrafluoroborate | | | |

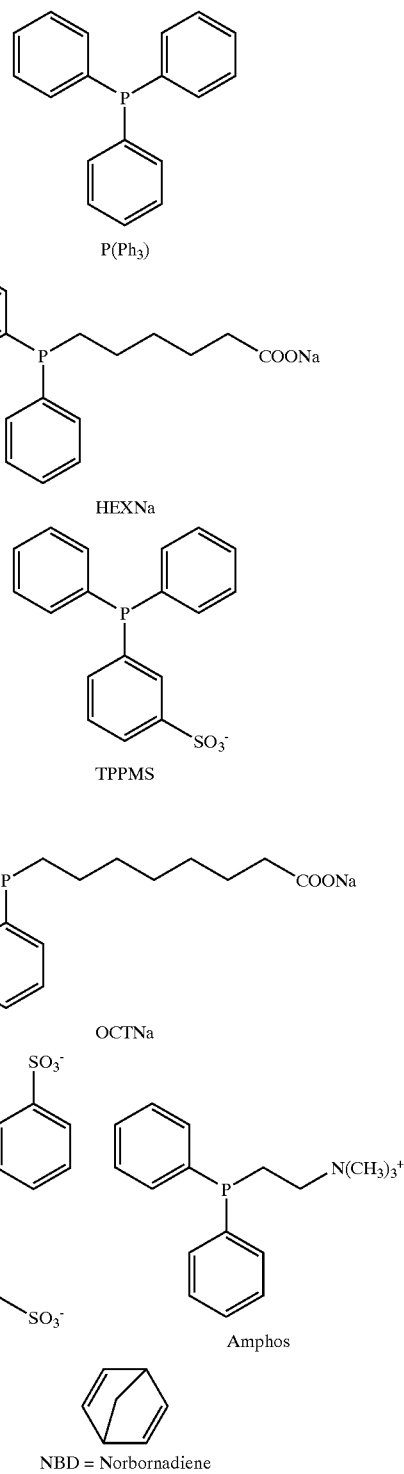

NBD = Norbornadiene

It has been found that rhodium catalysts are particularly useful in the hydrogenation step, most particularly those rhodium catalysts comprising phosphine groups.

The reaction mechanism of hydrogenation of ethylene with Wilkinson's catalyst is shown by way of example in FIG. 2. Reversibility of reaction is found to be low with such catalysts containing cyclic phosphines.

A further catalytic cycle is shown by way of example in FIG. 3. The oxidative addition of enriched hydrogen to the catalyst is generally an equilibrium step which means that certain catalysts will also interconvert p-H$_2$ and o-H$_2$. It is therefore desirable that the chosen hydrogenatable MR imaging agent precursor is highly reactive.

It is highly desirable to carry out the hydrogenation step in a very low magnetic field. Preferably this very low magnetic field is lower than the magnetic field of the earth itself, that is lower than 50 µT, more preferably less than 10 µT, even more preferably less than 2 µT, e.g. 0 to 1 µT, especially 0.3 to 1 µT. It is possible to create such low magnetic fields using, for example, commercially available magnetic shielding, for example µ-metal. The effect of the magnetic field on the degree of polarization of a reporter nucleus (in this case a $^{13}$C nucleus) is shown in FIG. 1.

It will be apparent that the degree of solubility of the hydrogenated MR imaging agent will determine how rapidly it can be dissolved in administrable media and subsequently administered and, given the finite lifetime of the polarisation, the importance of these factors will be clear. Thus hydrogenation is conveniently performed in aqueous media and preferred catalysts for use in the invention should operate efficiently in water and conveniently not facilitate the exchange of hydrogen atoms between water and the enriched hydrogen, otherwise the polarisation is quickly lost. A water soluble rhodium catalyst is one preferred example.

In order to facilitate rapid separation of catalyst and hydrogenated MR imaging agent after hydrogenation, the catalyst may preferably be one which is immobilized on a solid material e.g. a polymeric material which allows the catalyst-bound solid material to be rapidly filtered off after reaction. Known examples useful for the present method include catalysts covalently linked to a support or adsorbed on silica.

An alternative way to remove catalyst from an aqueous solution is to run the reaction in the presence of a water-soluble catalyst (e.g. a rhodium catalyst) which may then be removed by filtration through an ion-exchange resin or any other sort of filter that can retain the catalyst and allow the product to pass. In the preferred case of a cationic catalyst, filtration may be carried out through a cation exchanger. Particularly preferred catalysts are cationic rhodium catalysts. Rhodium catalysts transfer hydrogen as a unit to one substrate molecule and therefore avoid problems of H$_2$/D$_2$ scrambling. One such embodiment makes use of an ion-exchange resin bound cationic complex such as [(NBD)Rh (Amphos)$_2$]$^{3+}$. The aqueous solution of an anionic or neutral product is obtained in the filtrate. The opposite procedure may of course be used for anionic catalysts but these are generally less preferred. A neutral catalyst may be separated from the MR imaging agent by making use of physical characteristics such as lipophilicity. For example, a lipophilic catalyst (e.g. Wilkinson's catalyst) may be used in a biphasic system such as water/C18-derivatised silica or even two immiscible liquids such as water/heptane.

Hydrogenation may take place advantageously in a non-aqueous media in which the hydrogenation product is insoluble (i.e. from which it precipitates). The increased T$_1$ of the solid MR imaging agent allows more time for isolation and subsequent dissolution in an administrable medium. Hydrogenation may also take place with the MR imaging agent precursor being insoluble in non-aqueous media but with a particle size as small as possible to increase relative surface area. The use of non-aqueous media, preferably media with non-magnetically active nuclei (e.g. CS$_2$ or CO$_2$ under supercritical conditions) advantageously reduces polarisation loss from the polarised MR imaging agent and allows the use of an extended range of catalysts.

Viewed from another aspect the invention provides apparatus for hydrogenation comprising:
   a reaction chamber having therein a reaction zone, said reaction chamber having a gas inlet and a gas outlet;
   a temperature controller arranged to control the temperature in said reaction zone; and
   magnetic shielding arranged about said reaction zone and sufficient to cause the magnetic field in said reaction zone to be less than 10 µT, preferably less than 1 µT.

The reaction chamber will conveniently be disposed within a generally cylindrical µ-metal shield. This shield preferably has several concentric layers, e.g. a µ-metal layer of relatively high permittivity surrounded by a demagnetizing layer, e.g. of copper foil, and in turn surrounded by one or more layers of µ-metal of lower permittivity than the inner layer. The inner µ-metal layer is preferably of µ-metal of the highest available permittivity.

At each axial end, the cylindrical magnetic shield preferably extends in its axial direction beyond the reaction zone by at least the internal diameter of the shield. Although a circular cross-section is preferred, the cylindrical shield may be non-circular in cross-section, e.g. elliptical or polygonal, for example hexagonal. Where the cross-section is non-circular, the axial extension beyond the reaction zone is preferably by at least the minimum internal "diameter" (e.g. face to face spacing for a hexagonal cross section) but more preferably by at least the maximum internal diameter (e.g. corner to corner spacing for a hexagonal cross section).

The reaction zone may be for example comprise a bed of beads through which hydrogen may flow upwards from a lower gas inlet and through which a solution containing hydrogenatable precursor and hydrogenation catalyst may pass down to be removed from the reaction chamber through a lower product outlet. Alternatively, the beads may have the catalyst immobilized thereon so that the product solution is catalyst free and may be in a form ready to use. The beads are preferably formed from paramagentic material free polymer, glass or silica or are of a non-magnetic metal. Selection of bead size (e.g. 0.5 to 5 mm diameter, preferably 2 mm), bed depth and choice of direction of hydrogen flow will determine the duration of the reaction (generally 10 to 60 sec.). The preferred duration and bed depth can be determined by routine experimentation for the selected precursor/catalyst combination.

The temperature controller will conveniently be a heating/cooling jacket disposed about the reaction zone portion of the reaction chamber and within the shield. Preferably the materials used are non magnetic. A water- or gas-jacket is generally appropriate. A temperature sensor may be disposed in or adjacent the reaction zone if desired.

Conveniently, the reaction chamber has a precursor solution inlet above the reaction zone and an MR imaging agent solution outlet below the reaction zone. Thus in operation using this embodiment the following actions are performed:
   a source of pH$_2$ enriched hydrogen is attached to the gas inlet;
   the reaction chamber is flushed with the enriched hydrogen;
   water of the desired temperature is flowed through the water-jacket;
   a quantity of a solution, preferably a sterile aqueous solution, of the precursor compound is introduced into the reaction chamber and into a particulate bed through which the enriched hydrogen is flowing upwardly; and
   the solution passing out of the bed is withdrawn from the reaction chamber, optionally after reversal of hydrogen flow direction to drive the solution out of the bed.

Where the catalyst is not immobilized on the particles of the bed, it will generally be included in the precursor solution, either in dissolved or particulate or supported form. If desired the catalyst may be removed from the product solution, e.g. by precipitation and/or filtration or by passage over a material (e.g. an ion exchange column or lipophilic surface) which has affinity for the catalyst.

Catalyst removal clearly depends on the nature of the catalyst, the Precursor, the MR imaging agent and whether the subject to be imaged is a living human or animal or not. Thus for inanimate subjects, catalyst removal may be unnecessary. In one embodiment a hydrogenation catalyst soluble in a solvent that is imiscible with water is used and the hydrogenation reaction is carried out in water with a substrate that is soluble in organic solvents but has a distribution constant that favours water. The substrate is extracted into water that is injected i.v. In another embodiment a water-soluble polymer bound hydrogenation catalyst is used and the hydrogenation reaction is performed in water with a water-soluble substrate. The catalyst is removed by filtration prior to i.v. injection. In a third embodiment a solid polymer-bound hydrogenation catalyst is used and the hydrogenation reaction is performed in water with a water-soluble substrate. The catalyst is removed by filtration prior to i.v. injection. In a fourth embodiment a solid polymer-bound hydrogenation catalyst is used and the hydrogenation reaction is performed in water with a water-soluble substrate. The catalyst is removed by filtration prior to i.v. injection.

The withdrawal of the product solution is preferably by passage through a valve into the barrel of a syringe. The syringe may then be used to administer the MR imaging agent, e.g. by injection into a human or animal subject. The inner walls of the syringe and indeed of any apparatus components contacted by the hydrogenated MR imaging agent are preferably substantially free of paramagnetic (and ferro and ferrimagnetic) materials. Likewise the period of contact of the MR imaging agent with any surfaces between hydrogenation and administration should preferably be kept to a minimum.

In a preferred embodiment, the apparatus of the invention comprises:

(i) a reservoir of enriched hydrogen, preferably cooled, e.g. to liquid form;

(ii) a reaction chamber having a reaction zone containing a particulate bed and having a first gas inlet below said bed, a first gas outlet above said bed, a solution inlet above said bed and a solution outlet below said bed, and preferably a second gas inlet above said bed and optionally a second gas outlet below said bed (optionally since the solution outlet may function as a gas outlet);

(iii) a gas conduit from said reservoir to said first gas inlet in the reaction chamber, optionally provided with a heater to raise the temperature of gas flowing therethrough, and optionally provided with a valve to direct gas flow to said second gas inlet rather than to said first gas inlet;

(iv) a temperature controller, e.g. a water or gas jacket, disposed around said reaction chamber at at least said reaction zone; and (v) a magnetic shield disposed around said reaction chamber at at least said reaction zone.

The inlets and outlets to the reaction chamber are each preferably provided with a valve or if appropriate a septum and means for attaching vessels, e.g. the hydrogen reservoir, a syringe for receiving the MR imaging agent, a syringe containing the precursor solution, and reservoirs for receiving exhaust hydrogen (for recycling).

Such an apparatus may be set up near the MR imaging apparatus, e.g. so that the imaging agent may be manufactured "on-site" using reservoirs of $pH_2$ enriched hydrogen supplied from the, normally distant, location where the enriched hydrogen was prepared.

Alternatively, the apparatus may be arranged for a gas phase reaction with precursor and hydrogen being introduced into the reaction zone in gas form and with the exhaust gas being cooled to separate hydrogen (which will remain gaseous), precursor, MR imaging agent, and, the hydrogenation catalyst. With different boiling points, the imaging agent, precursor and if appropriate, the catalyst may be collected separately and removed for optional formulation (e.g. dissolution in an appropriate liquid medium) and administration in the case of the MR imaging agent and for recycling or subsequent reuse in the case of other components. The catalyst could be immobilized on a surface (e.g. the surface of beads in a bed or of capillaries in a bundle of parallel capillaries) or could be included in the gas flow as a gas or as entrained droplets or particles. To ensure adequate progression of the reaction, the reaction zone could be arranged in a spiral or the like within the magnetic shield and the reaction can be performed at elevated temperature and pressure. Apparatus comprising shielding, reaction chamber, temperature controller, gas inlets, MR imaging agent separator (e.g. a condenser) and gas outlet arranged for performing the hydrogenation in the gas phase forms a further aspect of the invention.

In one embodiment of the method of the invention, the polarised (hydrogenated) MR imaging agent may be stored at low temperature e.g. in frozen form. Generally speaking, at low temperatures the polarisation is retained longer and thus polarised MR imaging agents may conveniently be stored e.g. in liquid nitrogen. Prior to administration, the MR imaging agent may be rapidly warmed to physiological temperatures using conventional techniques such as infrared or microwave radiation.

Viewed from a further aspect the invention provides a physiologically tolerable MR imaging agent composition comprising an MR imaging agent together with one or more physiologically tolerable carriers or excipients, said imaging agent containing nuclei of a non-hydrogen I=½ isotope (e.g $^{13}C$, $^{15}N$ or $^{29}Si$), preferably at a higher than natural abundance, characterised in that said nuclei are polarized such that their nmr signal intensity is equivalent to a signal intensity achievable in a magnetic field of at least 0.1 T, more preferably at least 25 T, particularly preferably at least 100 T, especially preferably at least 450 T, e.g. at 21° C. in the same composition. Preferably the composition is sterile and is stable at a physiologically tolerable temperature (e.g. at 10–40° C.).

Polarization is given by the equation $$P = \left| \frac{N\alpha - N\beta}{N\alpha + N\beta} \right|$$

which at equilibrium is equal to $$\frac{1 - \exp(-\gamma \hbar B_o / kT)}{1 + \exp(-\gamma \hbar B_o / kT)}$$

where $N\alpha$ is the number of spins in nuclear spin state $\alpha$ (e.g. +½);

$N_\beta$ is the number of spins in nuclear spin state $\beta$ (e.g. −½);

γ is the magnetogyric ratio for the isotopic nucleus in question, e.g. $^{13}C$;

η is Planck's constant divided by 2π;

$B_o$ is the magnetic field;

k is Boltzmann's constant; and

T is temperature in kelvin.

Thus P has a maximum value of 1 (100% polarization) and a minimum value of 0 (0% polarization). For $^{13}C$ the maximum polarization obtainable by the low-field parahydrogen hydrogenation method corresponds to about 0.5 MT.

Given that the method of the invention should be carried out within the time that the MR imaging agent remains significantly polarised, once hydrogenation has occurred and if desired or necessary the catalyst has been removed, it is desirable for administration of the MR imaging agent to be effected rapidly and for the MR measurement to follow shortly thereafter. This means that the sample (e.g. body or organ) should be available close to the area in which the polarisation has been carried out. If this is not possible, the material should be transported to the relevant area at low temperature.

The preferred administration route for the MR imaging agent is parenteral, e.g. by bolus injection, by intravenous or intra-arterial injection or, where the lungs are to be imaged, by spray, e.g. by aerosol spray. Oral and rectal administration may also be used.

Where the MR imaging nucleus is other than a proton (e.g. $^{13}C$), there will be essentially no interference from background signals (the natural abundance of $^{13}C$, $^{15}N$, $^{29}Si$ etc. being negligible) and image contrast will be advantageously high. Thus the method according to the invention has the benefit of being able to provide significant spatial weighting to a generated image. In effect, the administration of a polarised MR imaging agent to a selected region of a sample (e.g. by injection) means that the contrast effect is, in general, localised to that region. The precise effect of course depends on the extent of. biodistribution over the period in which the MR imaging agent remains significantly polarised. In general, specific body volumes (i.e. regions of interest such as the vascular system) into which the MR imaging agent is administered may be defined with improved signal to noise properties of the resulting images in these volumes.

Moreover, the γ-factor of carbon is about ¼ of the γ-factor for hydrogen resulting in a Larmor frequency of about 10 MHz at 1 T. The rf-absorption in a patient is consequently and advantageously less than in $^1H$ imaging. A further advantage of MR imaging agents containing polarised $^{13}C$ nuclei is the ability to utilise large changes in chemical shift in response to physiological changes, e.g. pH or temperature.

In one preferred embodiment, a "native image" of the sample (e.g. body) may be generated to provide structural (e.g. anatomical) information upon which the image obtained in the method according to the invention may be superimposed. Such a native image is generally not available where the imaging nucleus is $^{13}C$ due to the low natural abundance of $^{13}C$ in the body. Thus the native image may be conveniently obtained as a proton MR image in an additional step to the method of the invention.

The MR imaging agent may be conveniently formulated with conventional pharmaceutical or veterinary carriers or excipients. MR imaging agent formulations manufactured or used according to this invention may contain, besides the MR imaging agent, formulation aids such as are conventional for therapeutic and diagnostic compositions in human or veterinary medicine but will be clean, sterile and free of paramagnetic, superparamagnetic, ferromagnetic or ferrimagnetic contaminants. Thus the formulation may for example include stabilizers, antioxidants, osmolality adjusting agents, solubilizing agents, emulsifiers, viscosity enhancers, buffers, etc. Preferably none of such formulation aids will be paramagnetic, superparamagnetic, ferromagnetic or ferrimagnetic. The formulation may be in forms suitable for parenteral (e.g. intravenous or intraarterial) or enteral (e.g. oral or rectal) application, for example for application directly into body cavities having external voidance ducts (such as the lungs, the gastrointestinal tract, the bladder and the uterus), or for injection or infusion into the cardiovascular system. However solutions, suspensions and dispersions in physiological tolerable carriers (e.g. water) will generally be preferred.

For use in in vivo imaging, the formulation, which preferably will be substantially isotonic, may conveniently be administered at a concentration sufficient to yield a 1 micromolar to 1 M concentration of the MR imaging agent in the imaging zone; however the precise concentration and dosage will of course depend upon a range of factors such as toxicity, the organ targeting ability of the MR imaging agent, and the administration route. The optimum concentration for the MR imaging agent represents a balance between various factors. In general, optimum concentrations would in most cases lie in the range 0.1 mM to 10 M, especially 0.2 mM to 1 M, more especially 0.5 to 500 mM. Formulations for intravenous or intraarterial administration would preferably contain the MR imaging agent in concentrations of 10 mM to 10 M, especially 50 mM to 500 mM. For bolus injection the concentration may conveniently be 0.1 mM to 10 M, preferably 0.2 mM to 10 M, more preferably 0.5 mM to 1 M, still more preferably 1.0 mM to 500 mM, yet still more preferably 10 mM to 300 mM.

Parenterally administrable forms should of course be sterile and free from physiologically unacceptable agents and from paramagnetic, superparamagnetic, ferromagnetic or ferrimagnetic contaminants, and should have low osmolality to minimize irritation or other adverse effects upon administration and thus the formulation should preferably be isotonic or slightly hypertonic. Suitable vehicles include aqueous vehicles customarily used for administering parenteral solutions such as Sodium Chloride solution, Ringer's solution, Dextrose solution, Dextrose and Sodium Chloride solution, Lactated Ringer's solution and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the MR imaging agents and which will not interfere with the manufacture, storage or use of the products.

Where the MR imaging agent is to be injected, it may be convenient to inject simultaneously at a series of administration sites such that a greater proportion of the vascular tree may be visualized before the polarisation is lost through relaxation. Intra-arterial injection is useful for preparing angiograms and intravenous injection for imaging larger arteries and the vascular tree.

The dosages of the MR imaging agent used according to the method of the present invention will vary according to the precise nature of the MR imaging agents used, of the tissue or organ of interest and of the measuring apparatus.

Preferably the dosage should be kept as low as possible whilst still achieving a detectable contrast effect. Typically the dosage will be approximately 10% of $LD_{50}$, eg in the range 1 to 1000 mg/kg, preferably 2 to 500 mg/kg, especially 3 to 300 mg/kg.

Once the MR imaging agent has been administered to the subject, the chosen procedures for detecting MR signals are that which is well known from conventional MR scanning. It is advantageous to use fast single shot imaging sequences e.g. EPI, RARE or FSE.

In conventional $^1$H-nmr imaging, the polarization which is responsible for the MR signal derives from the equilibrium polarization at the magnetic field of the primary magnet of the MR imaging apparatus. After an imaging sequence, this polarization (the magnetization in the z direction) is recovered by $T_1$ relaxation. By contrast where the MR signal derives from hyperpolarization of the reporter nuclei (e.g. $^{13}$C, $^3$He, $^{129}$Xe, $^{15}$N, $^{29}$Si, etc), the hyperpolarization cannot be recovered and the MR signal following a 90° RF pulse must be recovered by a train of 180° RF pulses.

Where however the hyperpolarization results from hydrogenation with parahydrogen the magnetization in the z direction is split into two populations with opposite signs (polarities) of magnetization, $+M_o$ and $-M_o$. In a preferred imaging sequence, after an 90° RF pulse, the 180° RF refocussing pulses should be timed such that the two components are parallel (in phase) at the echo time. This can be achieved by an initial delay of $\Delta\tau+\tau$ between the 90° RF pulse and the first 180° RF refocussing pulse with the subsequent 180° RF pulses occurring at a time separation TE=$2\tau$. $\Delta\tau$ here has the value $1/(2J)$ where J is the coupling constant for the reporter nucleus. A total of N 180° RF pulses will be required where N is the image matrix size in the phase-encoding direction. Signal detection occurs between the 180° RF pulses. Due to the coupling constant J, there are limitations on the length of the sampling time—if unwanted modulations, and hence ghosting in the phase direction of the image are to be avoided, the sampling time should not exceed $1/(4J)$. Typically the sampling time will be 1 to 8 ms. The inter-echo time should exceed the sampling time as little as technically possible to ensure maximum signal to noise. A schematic illustration of this imaging sequence is shown in FIG. 9.

In a standard CPMG-sequence, the 180° RF pulses are phase shifted $\pi/2$ relative to the 90° RF pulse, e.g. 90° x–180° y–180° y– . . . ; this arrangement is preferred for the imaging sequence described above.

Thus using an initial focussing delay makes it feasible to image a contrast agent with two anti parallel resonance lines as would be achieved by hydrogenation with para-hydrogen.

In an alternative approach, the problem can be addressed by applying 180° RF pulses (180° $RF_H$) at the proton frequency simultaneously with the 180° RF pulses (180° $RF_x$) at the reporter nucleus frequency. The effect of the 180° $RF_H$ pulse is to change the sign of he J-coupling so that this is not refocussed by the 180° $RF_x$ pulse. The echo signals from the two magnetization components will progressively begin to reinforce rather than cancel each other out and after sufficient such 180° $RF_H$ and 180° $RF_x$ pulses, the two magnetization components will be parallel (in phase). Thereafter no further 180° $RF_H$ pulses are required. The two components $+M_o$ and $-M_o$ will be in phase after time $T=1/(2J)$. If the spacing between the 180° $RF_H$ pulses is $2\tau$ then the number of 180° $RF_H$ pulses required is n where $2n\tau=1/(2J)$, ie. $n=1/4J\tau$). $\tau$ can be selected such that n is an integral number. Alternatively put, TE is set to $1/(2nJ)$.

In a standard CPMG-sequence, the 180° RF pulses are phase shifted $\pi/2$ relative to the 90° RF pulse. In the imaging sequence discussed above, which is a derivative of a RARE sequence, the 180° $RF_x$ pulses are of the same phase as the 90° $RF_x$ pulse.

Using this sequence, illustrated schematically in FIG. 17, the longitudinal magnetization is turned to the xy plane by a single 90° $RF_x$ pulse at the beginning of the sequence. Thus the full magnetization of the hyperpolarized reporter nuclei is available for generating an image. Compared to sequences using a train of low flip angle RF pulses the gain in signal to noise is approximately an order of magnitude. Moreover a signal may be obtained from a system with two antiparallel resonance lines, without need for asymmetric echoes (ie. where spin echoes and gradient echoes are not aligned). This is advantageous since the use of asymmetric echoes makes the imaging sequence sensitive to magnetic field inhomogeneities and results in image arcefacts.

Where a sequence based on a gradient echo pulse sequence and ultra low flip angles for RF pulses, the most commonly used sequence for hyperpolarized noble gases, is used for para-hydrogen hyperpolarized reporter nuclei, an echo time TE of $1/(2J)$ is required, resulting in a total acquisition time of $N/2J$ where N is the image matrix sign. Where n 180° $RF_H$ pulses are used to change the size of the J coupling and prevent refocussing of the J-coupling, the echo time is $1/(2nJ)$ and the image acquisition time $N/(2nJ)$, ie. a reduction by a factor of n. This reduction in scan time is beneficial as it reduces the signal loss due to $T_2$ relaxation. By way of example if the matrix size is 256 and the J-coupling is 25 Hz then the scan time for a single slice is more than 5 s if a gradient echo sequence is used. Where the imaging sequence of FIG. 9 is used, the total acquisition time is N ($2\tau$), which, depending on the imager, can be reduced to for example 0.5 to 2.5 seconds. By using the RARE-derivative sequence of FIG. 17 discussed above, the scan time can be reduced to 2.5 s (n=2) or 1.7 s (n=3), etc. (RARE sequences and sequences used in imaging hyperpolarized gases are described by Hennig et al. in Magn. Reson. Med 3:823–833 (1986) and Zhao et al. in Nucl. Instrum. and Meth. in Phys. Res. A402: 454–460 (1998)).

The method of the invention may also be used for $^1$H magnetic resonance imaging using the hydrogen hyperpolarisation introduced by para-hydrogen hydrogenation of an unsaturated bond. Here, imaging sequences which bring into phase the +Mo and −Mo magnetisation components are desirably used and the unsaturated bond is desirably between atoms which remain bonded together in the resulting MR imaging agent.

The contents of all publications referred to herein are hereby incorporated by reference.

Embodiments of the invention are described further with reference to the following non-limiting Examples and the accompanying drawings, in which.

Figure 1:
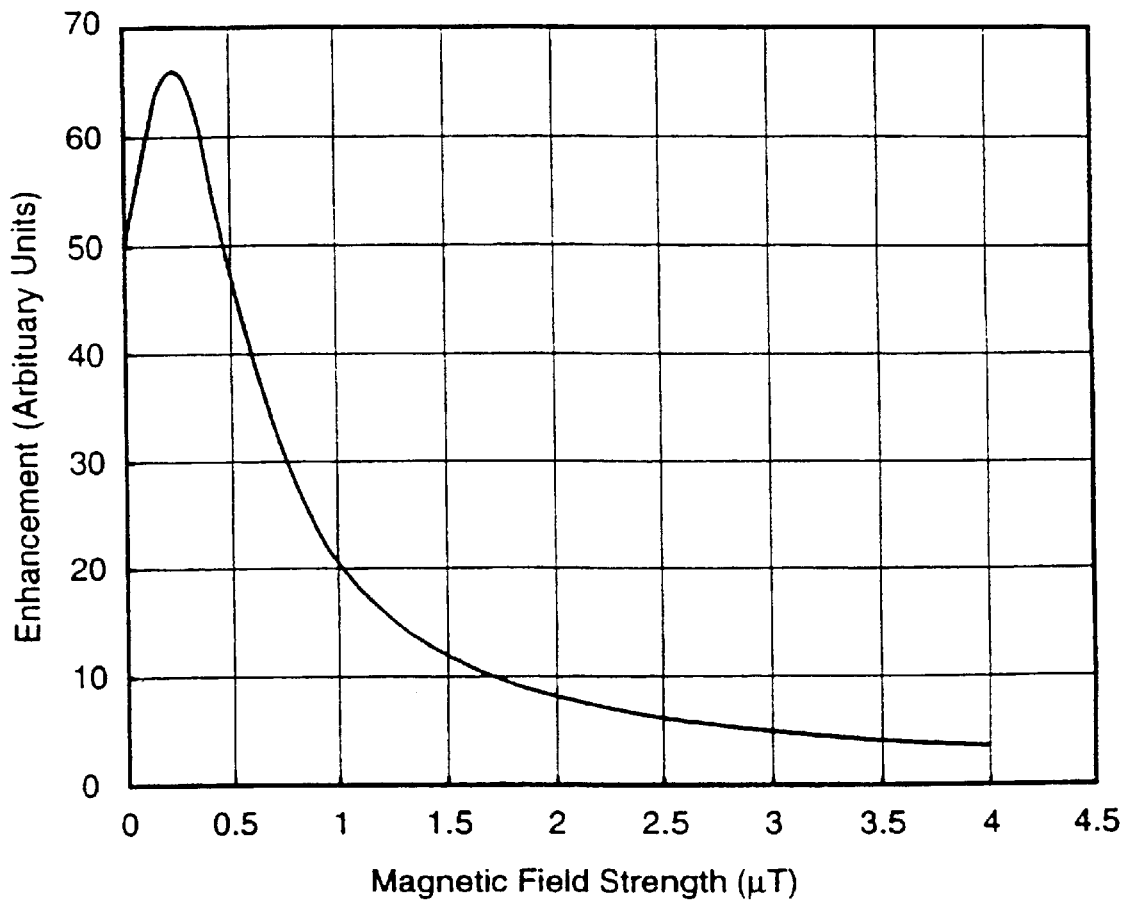
FIG. 1 is a clot of polarization enhancement of reporter nuclei (in an AA'x spin system with $J_{12}$=10.65 Hz, $J_{13}$=0.3 Hz and $J_{23}$=15.5 Hz) against the magnetic field strength at which hydrogenation with para-hydrogen enriched hydrogen occurs.
Figure 2:
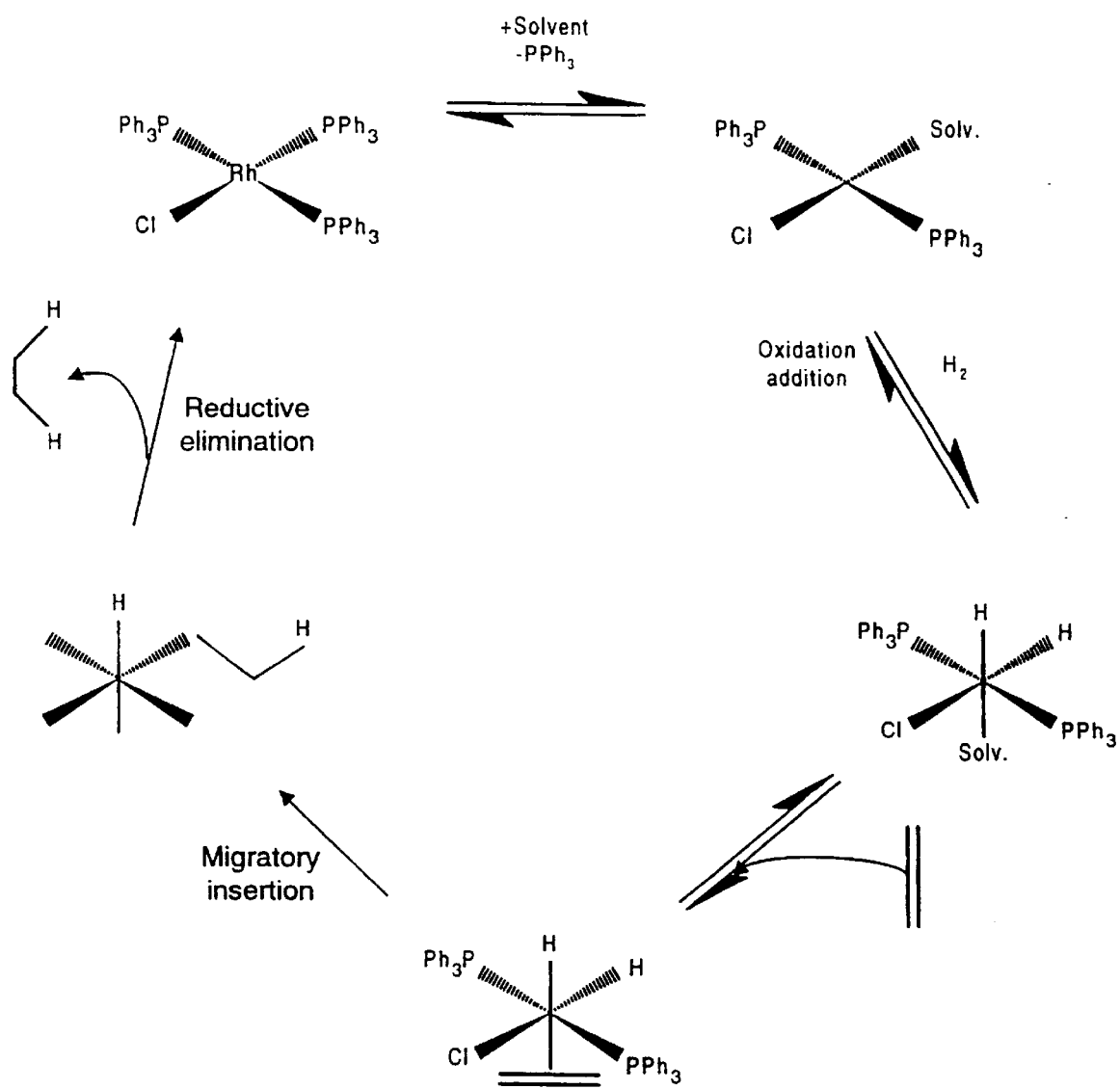
FIGS. 2 and 3 are reaction schemes for catalysed hydrogenation of precursor compounds.
Figure 3:
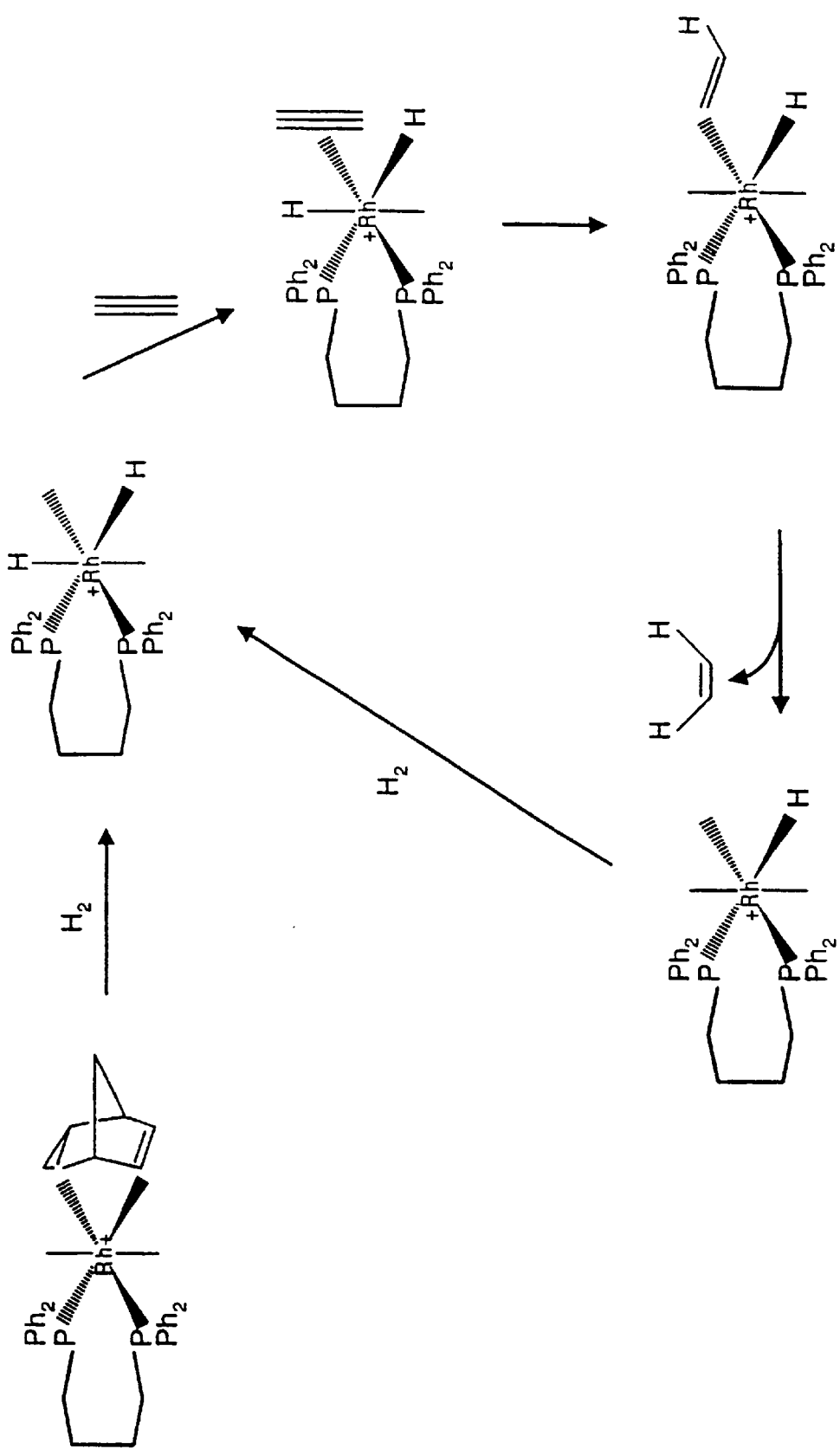
Figure 4:
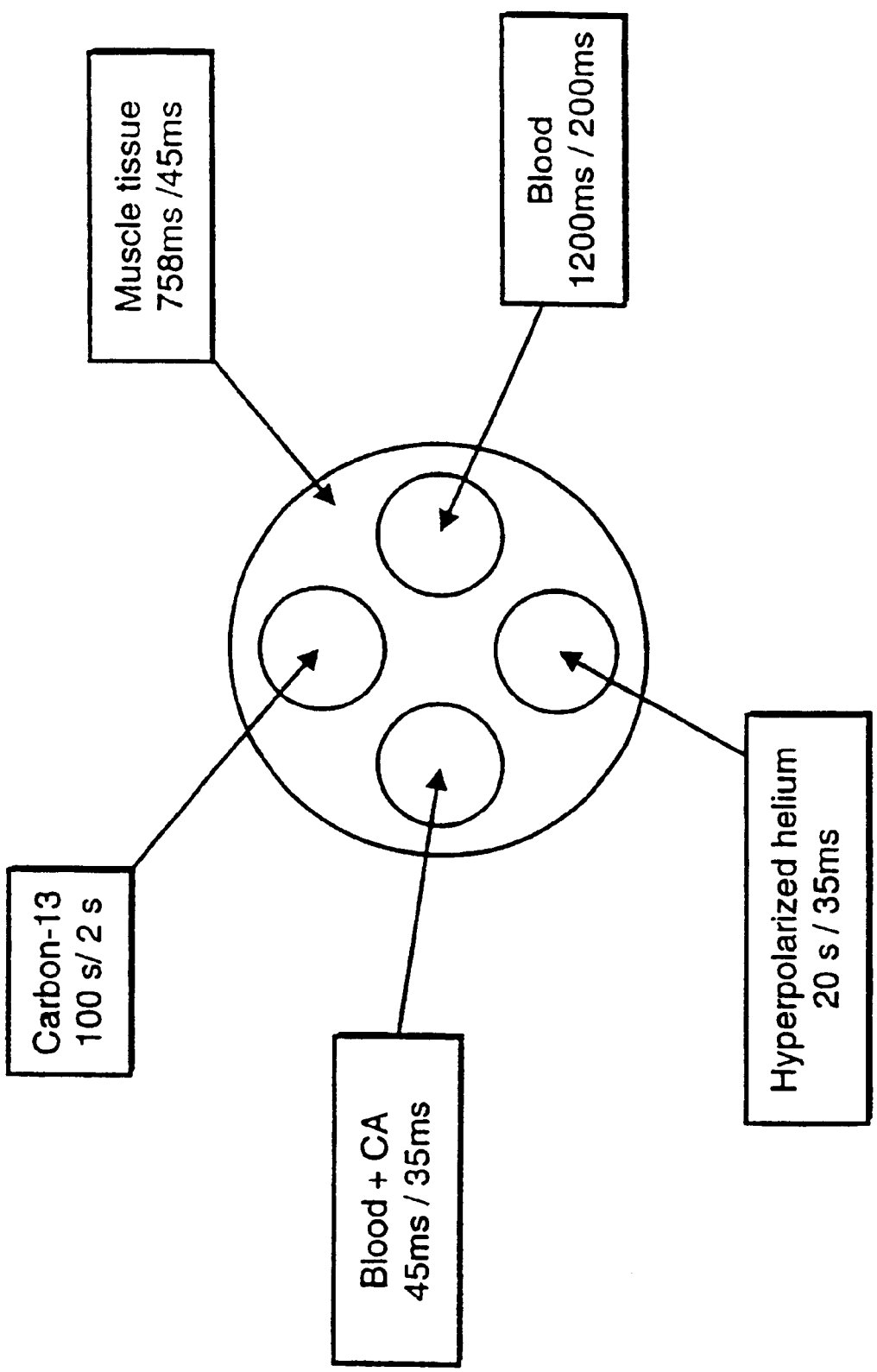
FIG. 4 is a diagram of a phantom.
Figure 5:
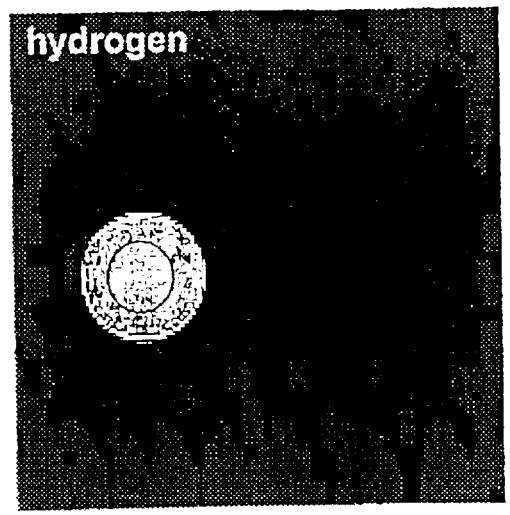
Figure 7:
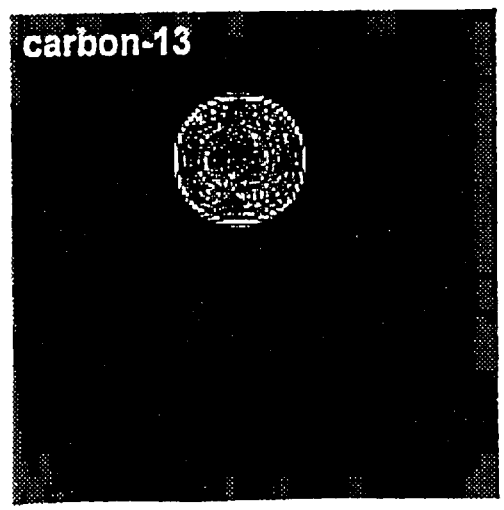
Figure 8:
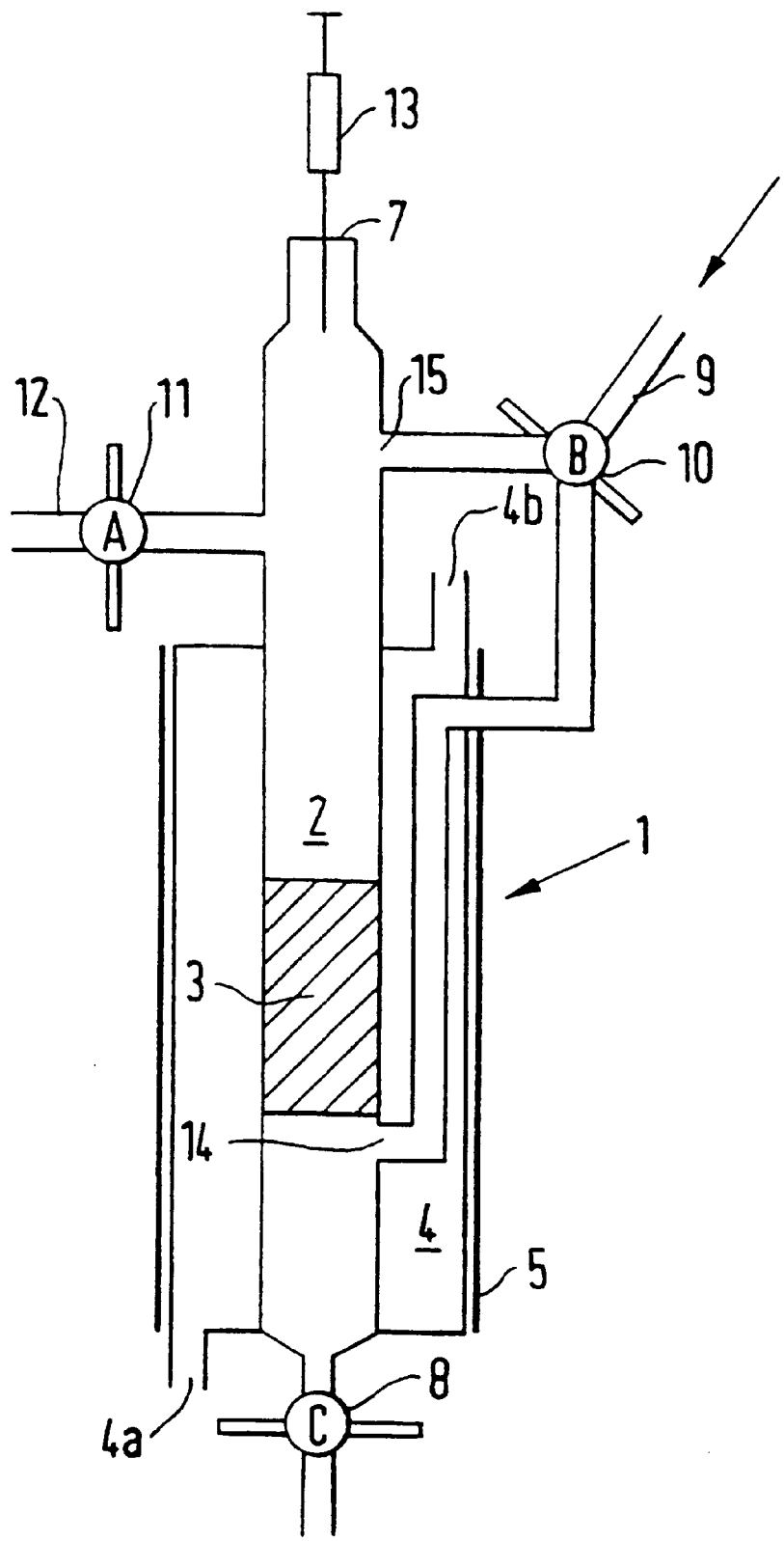
Figure 9:
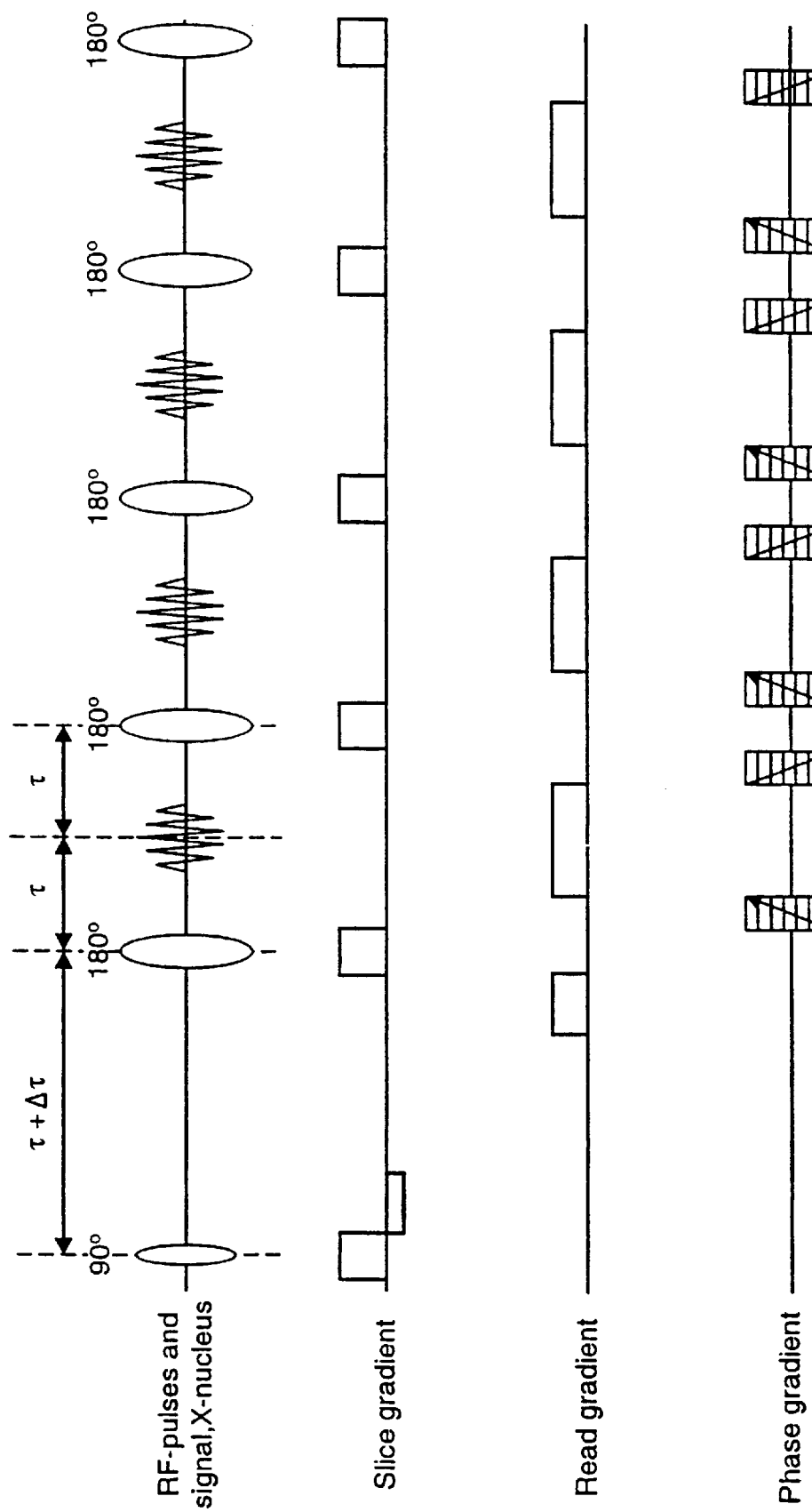
Figure 10:
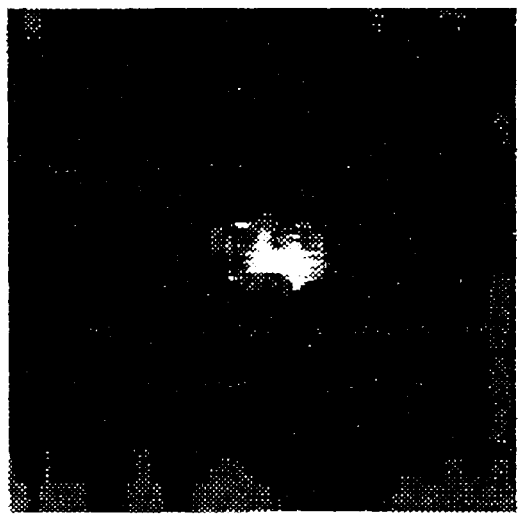
Figure 11:
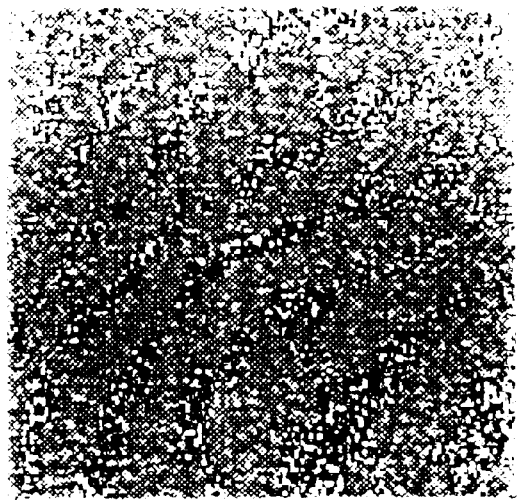
Figure 12:
Figure 13:
Figure 14:
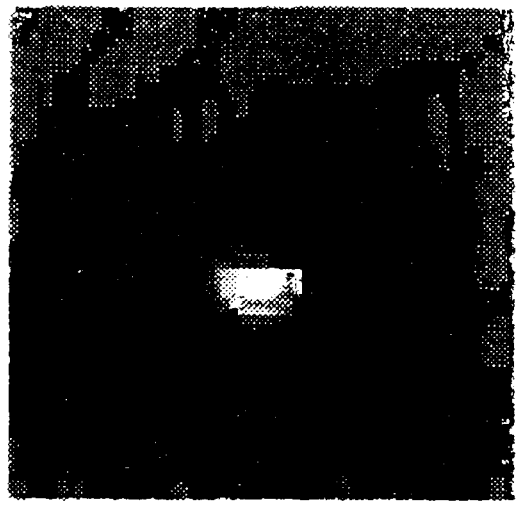
Figure 15:
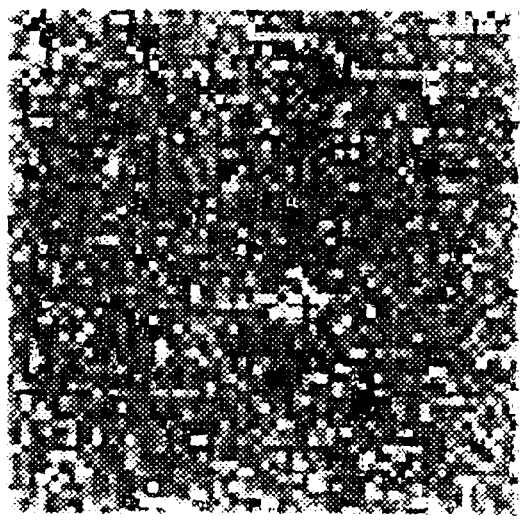
Figure 16:
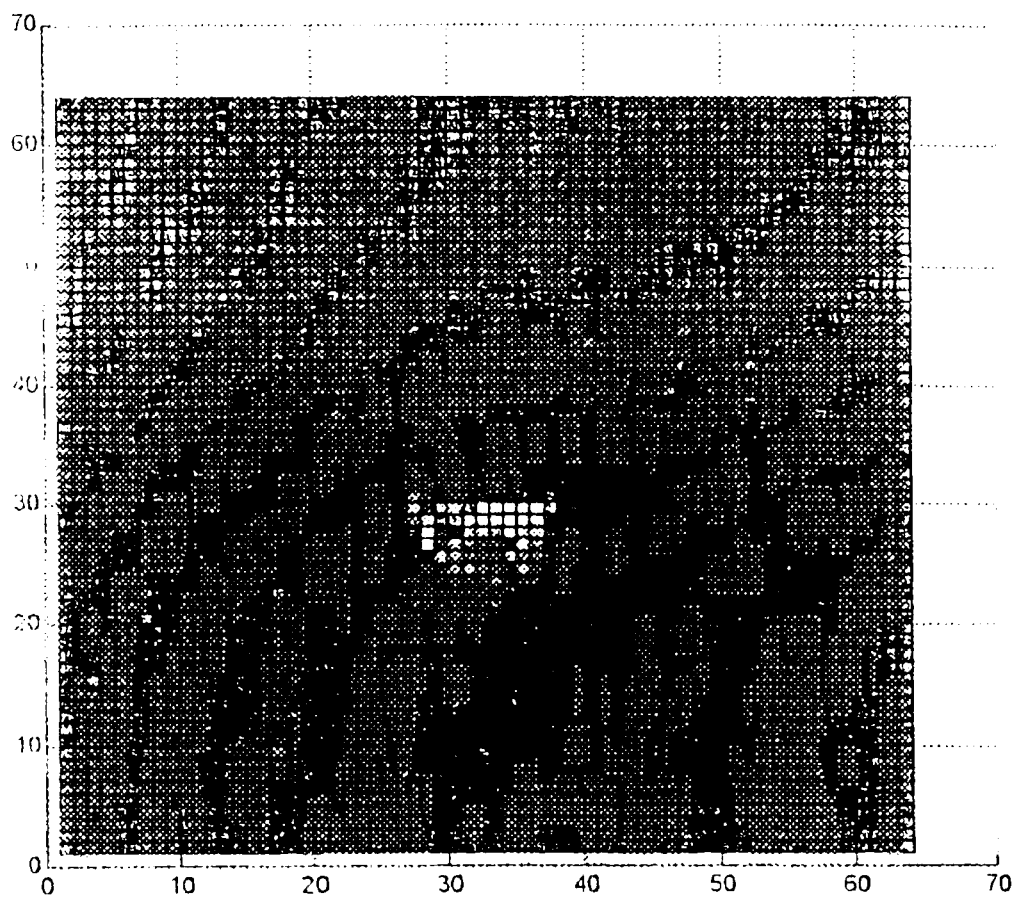
Figure 17:
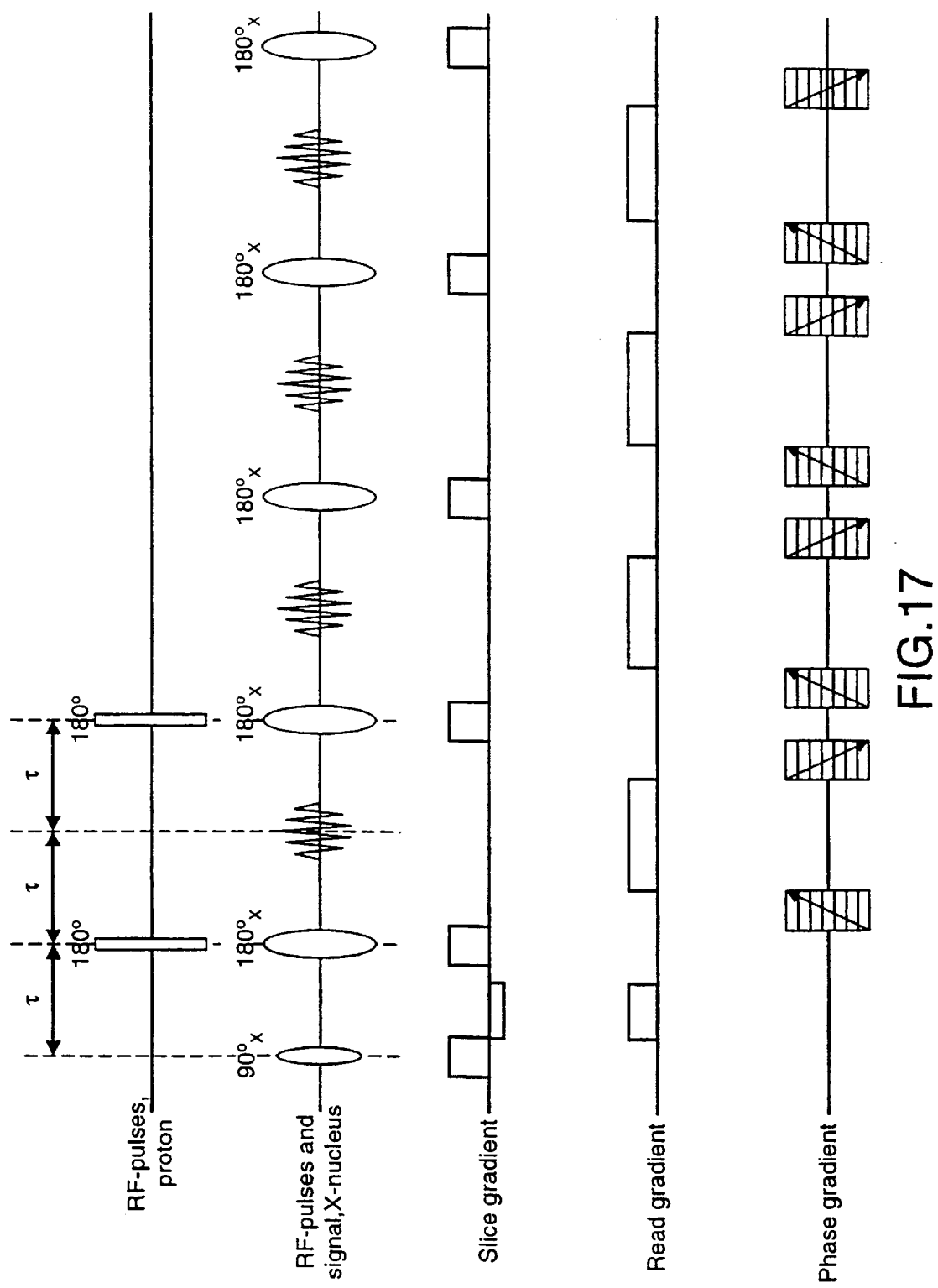

FIGS. 5, to 7 are simulated MR images of the phantom of FIG. 4;

FIG. 8 is a schematic representation of apparatus according to the invention for hydrogenation in a magnetically shielded reaction zone;

FIG. 9 is a schematic representation of a RARE derivative imaging sequence;

FIGS. 10 and 11 are $^{13}$C MR images of the rat stomach;

FIG. 12 is a $^1$H-MR image of the rat stomach;

FIG. 13 shows a superposition of a $^{13}$C-MR image of the rat stomach on a $^1$H MR image of the same;

FIG. 14 is a $^{13}$C-MR image obtained using a standard RARE-sequence of a phantom containing a constrast agent containing $^{13}$C at natural abundance and hydrogenated by para-hydrogen at low (microtesla) field;

FIG. 15 is an image corresponding to that of FIG. 12 but where hydrogenation was effected atearth field;

FIG. 16 is an image corresponding to that of FIG. 12 but where hydrogenation was effected atearth field and where the imaging sequence used is a modified RARE-derivative as discussed above; and FIG. 17 is a schematic illustration of a modified RARE imaging sequence.

Referring to FIG. 8, the hydrogenation apparatus 1 comprises a generally cylindrical glass reaction chamber 2, e.g. of 5 to 50 mm internal diameter, containing a bed 3 of glass beads defining a reaction zone and surrounded by thermostatted water jacket 4 having inlet 4a and outlet 4b and four-layer magnetic shield 5. The reaction chamber is closed at the top by a rubber septum 7 and is provided with an outlet valve 8 at its base. A para-hydrogen source (not shown) is attached to a gas conduit 9 which can lead into the reaction chamber above or below bed 3 depending on the position of valve 10. During hydrogenation, para-hydrogen may be vented from the reaction chamber through valve 11 and outlet 12. Precursor compound and catalyst may be introduced into the reaction chamber using a syringe 13 with a needle capable of piercing the septum.

Before use, water at 42° C. is circulated through the water jacket for at least 10 minutes. Valve 11 is opened, and valve 10 is put in position to allow para-hydrogen flow into the reaction chamber through the lower (14) of inlets 14 and 15. Valve 8 is closed. Flow of para-hydrogen is commenced. A flow of 130 mL/min is suitable where the reaction chamber internal diameter is 15 mm and the beads are 3 mm diameter. After 30 seconds, a solution of precursor and catalyst may be injected through septum 7. After the hydrogenation reaction is completed, e.g. after 40 seconds, valve 10 is moved to direct para-hydrogen flow into the reaction chamber through upper inlet 15, valve 8 is opened and valve 11 is closed. The solution passing out through valve 8 is collected.

EXAMPLE 1

An experiment was carried out to compare the expected SNR in (1) He-images generated using helium at 1 atm in lung tissue, (2) $^{13}$C-images generated using hyperpolarised H$_2$ and (3) "standard" contrast enhanced proton images. All calculations were performed using MRI-simulation software developed at Nycomed Innovation in Malmö Sweden. The calculation procedure is based on the k-space formalism (Petersson et al., 1993, Mag. Res. Imaging, 11: 557–568) and the multi dimensional description (Petersson et al., 1997, Mag. Res. Imagin, 15: 451–467) of the image formation in MRI.

A mathematically defined phantom according to FIG. 4 was used to input all calculations. The $^{13}$C was assumed to be in a bolus and the magnitude of the magnetization was raised to five times the magnitude used for hydrogen. 50% polarisation was assumed and the concentration was 45.0 mM. The relaxation times for $^{13}$C were $T_1$=100 s and $T_2$=2 s. The proton relaxation times are those found at 1.5 T. The blood containing contrast agent uses the relaxation times found when the bolus tracking technique is utilized. Hyperpolarised helium was assumed to be in form of a gas at 1 atm and the relaxation times were chosen in accordance with Bachert et al. Magn. Res. in Medicine, 36: 192–196 (1996) when the gas is present inside the lungs.

The short $T_2$ ($T_2^*$) is due to the high diffusion coefficient (D≈2 cm$^2$ s$^{-1}$). The magnitude of the helium magnetization was raised to 16 times that used for hydrogen. 50% polarisation was assumed and the concentration was 45.0 mM.

Two different pulse sequences were used. A fast gradient echo sequence, FLASH, was used to generate the hydrogen image and the helium image. The hydrogen pulse sequence parameters were TR/TE/α=8 ms/2 ms/30° and the helium pulse sequence was 8 ms/2 ms/3°. The enhancement gain of the He-magnetization is in this way divided during the imaging process.

A RARE (Fast Spin Echo) sequence was used to generate the $^{13}$C image. Eight interleaves were used in order to simulate the situation found when imaging the heart using gating. The $^{13}$C magnetization behaved the same way as the He magnetization i.e. no new magnetization was generated due to $T_1$-relaxation during the imaging process. During the calculation the $^{13}$C were modelled in the form of a bolus and between the interleave in the pulse sequence the excited magnetization was replaced with fresh magnetization. If a static object was imaged the sequence could have been performed as a single shot sequence without (due to the long $T_2$ value) any loss in signal amplitude.

RESULTS

Hydrogen

In the proton image (FIG. 5), the helium and the $^{13}$C do not show up. The signal from the blood and contrast agent appears bright. The short TR and the relatively high flip angle makes the image strongly $T_1$-weighted. The muscle and the blood without contrast agent appears dark. The signal amplitude in the ROI was 129 and SNR=107.

Heliumn

Figure 6:
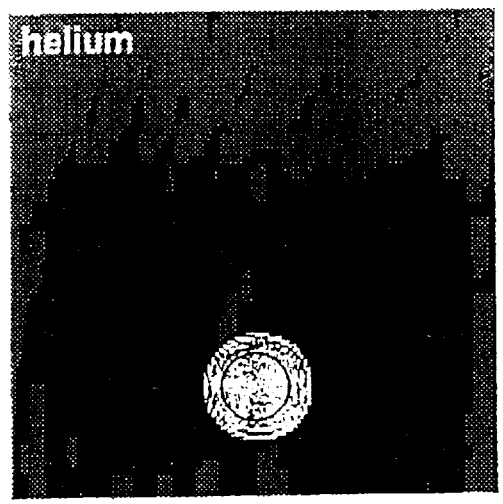

In the He-image (FIG. 6) the proton and $^{13}$C do not show up. The signal from the helium appears bright and no background from other tissues are present. The short TR and the relatively low flip angle generated an image which in normal proton imaging would be considered as a spin density image. The signal amplitude in the ROI was 347 and SNR=289.

Carbon-13

In the $^{13}$C image (FIG. 7) the protons and the helium do not show up. The signal from $^{13}$C appears bright and no background from other tissues is present. The selected RARE sequence may be considered $T_2$-weighted. The image was generated using a multi shot technique but a single shot version would (due to the long $T_2$-value) result in the same signal amplitude. The signal amplitude in the ROI was 2605 and SNR=1737.

Conclusion

The generated signal amplitude and SNR values indicate the already recognised utility of helium as a contrast agent in lung imaging. If the gas was dissolved in blood the signal amplitude would drop considerably (Martin et al., J. Mag. Res. Imaging, 1997, 7, 848–851). The $^{13}$C image indicated that when the polarisation of enriched hydrogen is transferred to a $^{13}$C-atom in a suitable organic molecule images with high SNR may be generated. Due to the long $T_1$ and $T_2$, modern fast single shot sequences may be used. Whilst the $^{13}$C-fluid behaves as a bolus the long $T_1$ will make it possible to reach the heart with only a moderate loss in signal amplitude even if it is administered by i.v. injection.

EXAMPLE 2

The following reactions are performed and produce the enhancement effects mentioned.

(A) Ph—C≡CH+para-hydrogen and homogeneous rhodium catalyst (giving $^1$H enhancement of about 200 and 20% conversion in about 20 seconds).

(B) EtOOC—C≡C—COOEt+para-hydrogen and homogeneous rhodium catalyst, converting about 100% in about 20 seconds to the cis C=C product and giving $^{13}$C enhancement of about×500.

(C) R—CH=CH—COOH+para-hydrogen and a resin bound rhodium catalyst in water, converting about 75% in 8 minutes to RCH$_2$CHCOOH (where R is H or COOH).

EXAMPLE 3

Low-field Enhancement of the Para-hydrogen Signal

Acetylene dicarboxylic acid dimethyl ester (0.5 g) with a natural abundance of $^{13}$C, and (bicyclo[2.2.1]hepta-2,5-diene)[1,4-bis(diphenylphosphino)butane]rhodium(I) tetrafluoroborate (0.12 mmol) in a solution of deuteroacetone (5 ml) was hydrogenated with hydrogen gas enriched in para-hydrogen (50%) for 40 seconds with a jacket temperature of 42° C. in the hydrogenation reactor described above in connection with FIG. 8 with the magnetic screen in place.

The solution was transferred to an nmr-tube and, following a 90° pulse, a spectrum was recorded at the $^{13}$C frequency in a 7 T NMR-spectrometer within 20 seconds after the reaction was finished. The intensity of the signal was compared to a standard sample and was found to be 1500 times the thermodynamic signal at 25° and 7T. It was necessary to detune the NMR-probe significantly to be able to perform proper excitations on such a highly polarized sample.

In another experiment the sample solution was transferred to a glass vial and imaged using a standard RARE-sequence. The result is shown in FIG. 14. As a comparison a new sample was hydrogenated in ambient field (80 micro-Tesla) and subjected to the same imaging scheme. No signal could be detected. The result is shown in FIG. 15.

EXAMPLE 4

Imaging of the Para-hydrogen Enhanced Signal in Phantoms

Acetylene dicarboxylic acid dimethyl ester (6 mmol) with a natural abundance of $^{13}$C, and (bicyclo [2.2.1]hepta-2,5-diene)[1,4-bis(diphenyiphosphino)butane]rhodium(I) tetrafluoroborate (0.23 mmol) in a solution of deuteroacetone (10 ml) was hydrogenated with hydrogen gas enriched in para-hydrogen (50%) for 40 seconds with a jacket temperature of 42° C. in the hydrogenation reactor described above in connection with FIG. 8 with the magnetic screen removed.

The sample was transferred to a vial and placed in the magnet of an imaging magnet and a picture was recorded within 30 seconds after the reaction was finished. After Fourier transform, the image shown in FIG. 16 was obtained and after calibration with a standard sample the signal enhancement was calculated to be 225 times the polarization obtained at equilibrium at 2.4 T and 20° C. The special pulse sequence described above and shown schematically in FIG. 9 was used (90x–19.2 ms, 5 ms–(180y–10 ms)×64). The focusing delay was set to 19.2 ms and the inter-echo delay was set to 10 ms.

EXAMPLE 5

Imagine of the Para-hydrogen Enhanced Sianal in Rat

Acetylenene dicarboxylic acid dimethyl ester-1-$^{13}$C (99%) (6 mmol), and (bicyclo[2.2.1]hepta-2,5-diene)[1,4-bis(diphenylphosphino)butane]rhodium(I) tetrafluoroborate (0.23 mmol) in a solution of deuteroacetone (10 ml) was hydrogenated with hydrogen gas enriched in para-hydrogen (50%) for 40 seconds with a jacket temperature of 42° C. in the hydrogenation reactor described above in connection with FIG. 8 with the magnetic screen removed.

The hydrogenated sample was transferred to a syringe and injected into the stomach of a rat. The rat was then placed in the imaging magnet and a picture was recorded using the same pulse sequence as above. As a reference, She proton image of the rat in the same position was also obtained. A control experiment where the pulse sequence was repeated after relaxation of the contrast agent was also performed. No image could be detected in this case. The results are shown in FIGS. 10 to 13.

What is claimed is:

1. A method of magnetic resonance investigation of a sample, said method comprising:

(i) reacting para-hydrogen enriched hydrogen with a hydrogenatable MR imaging-agent precursor comprising a non-hydrogen non zero nuclear spin nucleus to produce a hydrogenated MR imaging agents;

(ii) administering said hydrogenated MR imaging agent to said sample;

(iii) exposing said sample to radiation of a frequency selected to excite nuclear spin transitions of said non-zero nuclear spin nucleus in said hydrogenated MR imaging agent;

(iv) detecting magnetic resonance signals of said non-zero nuclear spin nucleus from said sample; and (v) optionally, generating an image or biological functional data or dynamic flow data from said detected signals.

2. A method as claimed in claim 1 wherein said enriched hydrogen has a more than 45% proportion of para-hydrogen.

3. A method as claimed in claim 1 wherein said MR imaging agent precursor comprises nuclei selected from F, Li, C, N, Si and P nuclei.

4. A method as claimed in claim 3 wherein said non-zero nuclear spin nucleus is $^{13}$C.

5. A method as claimed in claim 1 wherein said non-zero nuclear spin nucleus is present at a level greater than its natural isotopic abundance.

6. A method as claimed in claim 1 wherein said precursor comprises a hydrogenatable unsaturated carbon-carbon bond.

7. A method as claimed in claim 1 wherein in said MR imaging agent the coupling constant (J) between said non-zero spin nucleus and a proton deriving from para-hydrogen is between 10 and 100 Hz.

8. A method as claimed in claim 7 wherein the nmr signal from said non-zero nuclear spin nucleus in said MR imaging agent has a line width of less than 10 Hz.

9. A method as claimed in claim 1 wherein said MR imaging agent is water-soluble.

10. A method as claimed in claim 1 wherein the chemical shift and/or the coupling constant of said non-zero nuclear spin nucleus in said MR imaging agent is sensitive to the physicochemical environment of said agent.

11. A method as claimed in claim 10 wherein said non-zero nuclear spin nucleus in said MR imaging agent is sensitive to pH and wherein said signals are manipulated to produce an image or data indicative of pH.

12. A method as claimed in claim 1 wherein step (i) is effected in a magnetic field smaller than the earth's ambient field, preferably a magnetic field of less than 10 $\mu$T.

13. A method as claimed in claim 1 wherein in step (iii) said sample is exposed to a 90° pulse of radiation of a frequency selected to excite nuclear spin transitions of said non-zero nuclear spin nucleus followed by 180° pulses of said radiation, where the time interval between said 180° pulses is 2$\tau$ and the time interval between said 90° pulse and the subsequent 180° pulse is $\tau$ plus $\Delta\tau$ where $\Delta\tau$ is 1/(2J) where J is the coupling constant of said non-zero nuclear spin nucleus in said MR imaging agent.

14. A method as claimed in claim 1 wherein in step (iii) said sample is exposed to a 90° pulse of radiation of a frequency selected to excite nuclear spin transitions of said non-zero nuclear spin nucleus followed at time intervals of 2$\tau$ by 180° pulses of said radiation of the same phase and where for the first n said 180° pulses said sample is simultaneously exposed to 180° pulses of radiation of a frequency selected to excite proton nuclear spin transitions, the relation between n and $\tau$ being $\tau=1/(4nJ)$ where J is the coupling constant of said n on-zero nuclear spin nucleus in said MR imaging agent.

15. The method of claim 1 wherein said hydrogenatable MR imaging agent precursor is a precursor compound:
  (i) comprising a hydrogenatable unsaturated bond;
  (ii) comprising a non-hydrogen non zero nuclear spin nucleus at greater than natural isotopic abundance;
  (iii) having a molecular weight below 1000 D; and
  (iv) which following hydrogenation has an nmr spectrum for said non-hydrogen non zero nuclear spin nucleus which is a multiplet having a coupling constant relative to one of the hydrogens introduced by hydrogenation of 1 to 300 Hz and having a linewidth of less than 100 Hz, and wherein when said precursor compound is a $^{13}$C enriched compound then said nucleus is a quaternary carbon nucleus.

16. The method of claim 15 wherein said precursor compound comprises the following molecular sub-units:
  (i) at least one C=C or C≡C bonds;
  (ii) a C, N or Si atom separated by one or two bonds from a C=C or C≡C bond, bound only to atoms the naturally most abundant isotopic form of which has a nuclear spin I=0, and not coupled by a series of covalent bonds to any atoms the naturally most abundant isotopic form of which has I>½; and
  (iii) at least one water-solubilizing moiety, ie. a functional group which imparts water solubility to the molecule.

17. The method of claim 1 wherein said precursor compound is hydrogenated with said hydrogen to produce a reporter compound:
  (i) comprising at least two protons;
  (ii) comprising a non-hydrogen non zero nuclear spin nucleus at greater than natural isotopic abundance;
  (iii) having a molecular weight below 1000 D; and
  (iv) having an nmr spectrum for said non-hydrogen non zero nuclear spin nucleus which is a multiplet having a coupling constant relative to one of said at least two protons 1 to 300 Hz and having a linewidth of less than 100 Hz,
    and wherein when said reporter compound is a $^{13}$C enriched compound then said nucleus is a quaternary carbon nucleus.

18. The method of claim 17 wherein said reporter compound comprises the following molecular sub-units:
  (i) at least one CH—CH or CH=CH moiety;
  (ii) a C, N or Si atom separated by one or two bonds from a CH—CH or CH=CH moiety, bound only to atoms the naturally most abundant isotopic form of which has I=0, and not coupled by a series of covalent bounds to any atoms the naturally most abundant isotopic form of which has I>½; and
  (iii) at least one water-solubilizing moiety, ie. a functional group which imparts water solubility to the molecule.

19. The method of claim 1 wherein said hydrogenated MR imaging agent which is administered is a physiologically tolerable MR imaging agent composition comprising said MR imaging agent together with one or more physiologically tolerable carriers or excipients, said imaging agent containing non-hydrogen nuclei having a nuclear spin of ½, characterised in that said nuclei are polarized such that their nmr signal intensity is equivalent to a signal intensity achievable in a magnetic field of at least 0.1 T.

20. The method of claim 19 wherein said nucleus is present in an amount in excess of its natural isotopic abundance.

21. An apparatus for hydrogenation comprising:
  a reaction chamber having therein a reaction zone, said reaction chamber having a gas inlet and a gas outlet;
  a temperature controller arranged to control the temperature in said reaction zone; and
  magnetic shielding arranged about said reaction zone and sufficient to cause the magnetic field in said reaction zone to be less than 10 $\mu$T.

22. Apparatus as claimed in claim 1 comprising:
  (i) a reservoir of para-hydrogen enriched hydrogen;
  (ii) a reaction chamber having a reaction zone containing a particulate bed and having a first gas inlet below said bed, a first gas outlet above said bed, a solution inlet above said bed and a solution outlet below said bed;
  (iii) a gas conduit from said reservoir to said first gas inlet in the reaction chamber;
  (iv) a temperature controller disposed around said reaction chamber at at least said reaction zone; and
  (v) a magnetic shield disposed around said reaction chamber at at least said reaction zone.

* * * * *